United States Patent [19]
Edwards et al.

[11] Patent Number: 5,871,443
[45] Date of Patent: *Feb. 16, 1999

[54] CARDIAC MAPPING AND ABLATION SYSTEMS

[75] Inventors: Stuart D. Edwards, Los Altos; Thomas F. Kordis, Sunnyvale; David K. Swanson, San Jose, all of Calif.

[73] Assignee: EP Technologies, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 747,811

[22] Filed: Nov. 14, 1996

Related U.S. Application Data

[62] Division of Ser. No. 636,174, Apr. 22, 1996, abandoned, which is a division of Ser. No. 168,476, Dec. 16, 1993, Pat. No. 5,509,419, which is a division of Ser. No. 951,157, Sep. 25, 1992, Pat. No. 5,309,910.

[51] Int. Cl.⁶ .................................. A61B 5/04; A61N 1/05
[52] U.S. Cl. ............................................................ 600/374
[58] Field of Search ............................. 128/642; 607/122, 607/116, 119, 123, 126, 128, 130; 606/41; 600/373, 374, 375

[56] References Cited

U.S. PATENT DOCUMENTS

| | | |
|---|---|---|
| 3,326,207 | 6/1967 | Egan . |
| 3,517,128 | 6/1970 | Hines . |
| 3,557,794 | 1/1971 | VanPatten . |
| 3,890,977 | 6/1975 | Wilson . |
| 4,360,031 | 11/1982 | White . |
| 4,444,195 | 4/1984 | Gold . |
| 4,461,302 | 7/1984 | Kuperstein . |
| 4,522,212 | 6/1985 | Gelinas et al. . |
| 4,573,473 | 3/1986 | Hess . |
| 4,592,373 | 6/1986 | Beranek . |
| 4,628,937 | 12/1986 | Hess et al. . |
| 4,630,611 | 12/1986 | King . |
| 4,641,649 | 2/1987 | Walinsky et al. . |
| 4,649,924 | 3/1987 | Taccardi . |
| 4,649,938 | 3/1987 | McArthur . |
| 4,660,571 | 4/1987 | Hess et al. . |
| 4,664,120 | 5/1987 | Hess . |
| 4,681,117 | 7/1987 | Brodman et al. . |
| 4,690,148 | 9/1987 | Hess . |
| 4,690,155 | 9/1987 | Hess . |
| 4,699,147 | 10/1987 | Chilson et al. . |
| 4,784,133 | 11/1988 | Mackin . |
| 4,862,887 | 9/1989 | Weber et al. . |
| 4,882,777 | 11/1989 | Narula . |
| 4,890,623 | 1/1990 | Cook et al. . |
| 4,892,102 | 1/1990 | Astrinsky . |
| 4,928,695 | 5/1990 | Goldman et al. . |
| 4,940,064 | 7/1990 | Desai . |
| 4,944,088 | 7/1990 | Doan et al. . |

FOREIGN PATENT DOCUMENTS

| 4025369 | 2/1991 | Germany . |
|---|---|---|

OTHER PUBLICATIONS

"Linear and Non–Linear Superelasticity in NiTi"; Zadno et al., MRS Int'l Mtg. on Adv. Mats. vol. 9, 1989, Materials Research Society, pp. 201–206.

"An Engineer's Perspective of Pseudoelasticity", Duerig et al., Engineering Aspects of Shape Memory Alloys, Butterworth–Heinemann, Pub. 1990, pp. 369–393.

*Primary Examiner*—Jeffrey R. Jastrzab
*Attorney, Agent, or Firm*—Lyon & Lyon LLP

[57] ABSTRACT

An electrode assembly for use in interventricular cardiac mapping includes one or more elongated splines each of which carries a plurality of spaced apart electrodes thereon. The body of each spline is formed of a plurality of alternating electrically conductive layers and the electrically non-conductive layers. A separate electrically conductive pathway is provided to connect each of the electrodes to a different one of the conductive layers. Each of the layers is electrically connected to an electrical signal processing device so that signals provided by each of the electrodes can be processed.

16 Claims, 20 Drawing Sheets

U.S. PATENT DOCUMENTS

| | | |
|---|---|---|
| 4,945,912 | 8/1990 | Langberg . |
| 4,974,162 | 11/1990 | Sigel et al. . |
| 4,976,710 | 12/1990 | Mackin . |
| 4,979,510 | 12/1990 | Franz et al. . |
| 5,010,894 | 4/1991 | Edhag . |
| 5,025,786 | 6/1991 | Siegel . |
| 5,029,585 | 7/1991 | Lieber et al. . |
| 5,041,973 | 8/1991 | Lebron et al. . |
| 5,045,056 | 9/1991 | Behl . |
| 5,056,517 | 10/1991 | Fenici . |
| 5,127,421 | 7/1992 | Bush et al. . |
| 5,156,151 | 10/1992 | Imran . |
| 5,237,996 | 8/1993 | Waldman et al. . |
| 5,255,679 | 10/1993 | Imran . |
| 5,411,025 | 5/1995 | Webster, Jr. . |

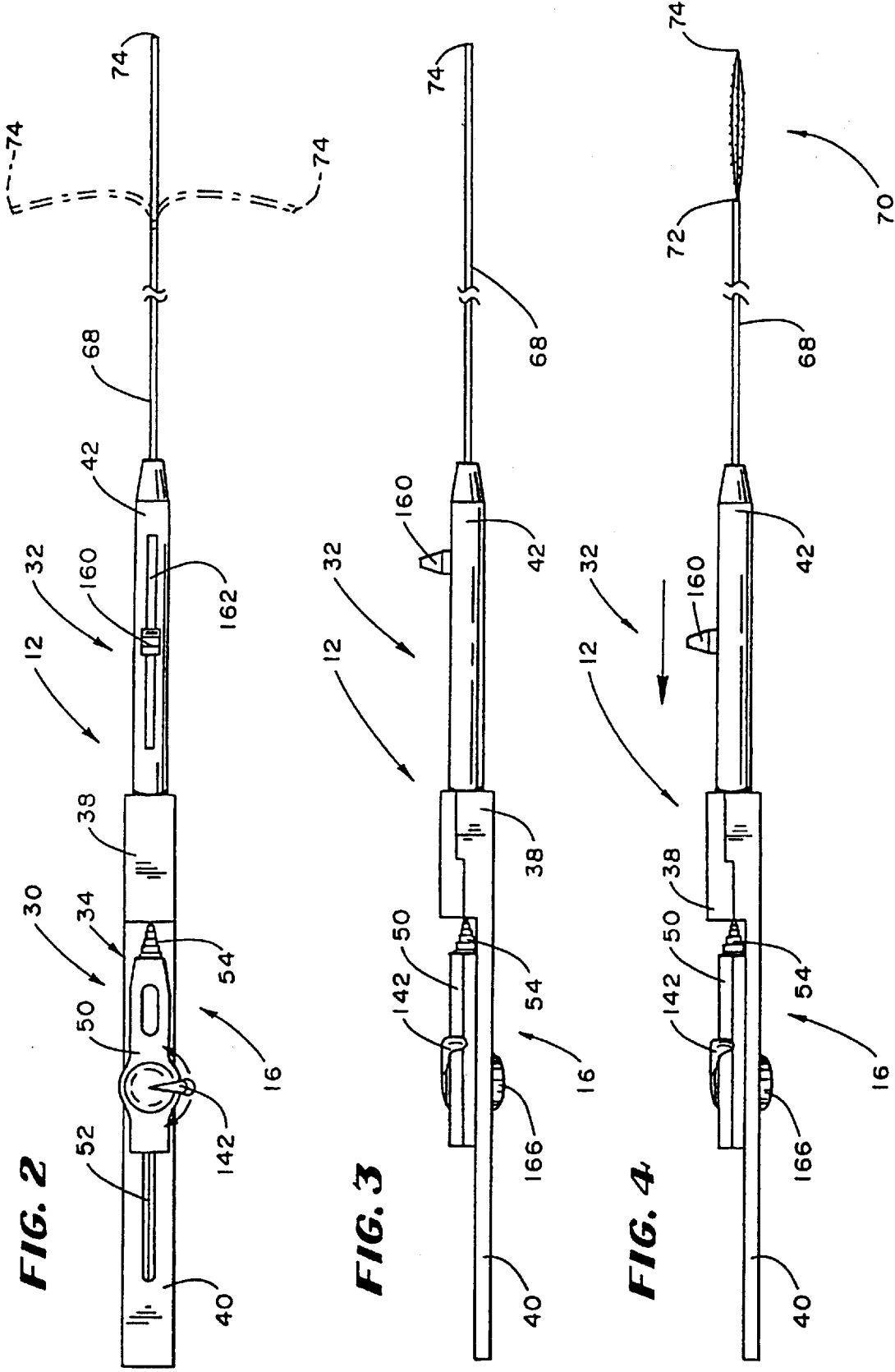

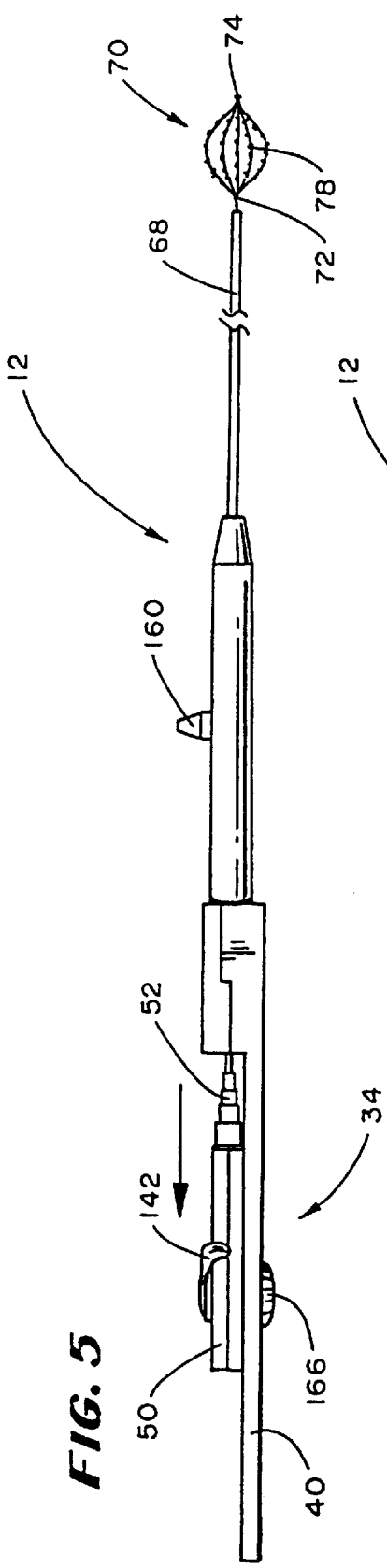
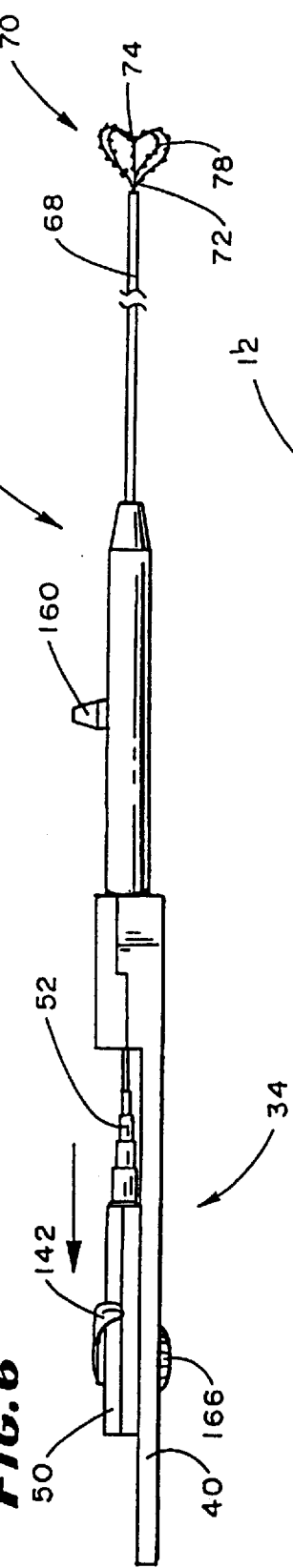
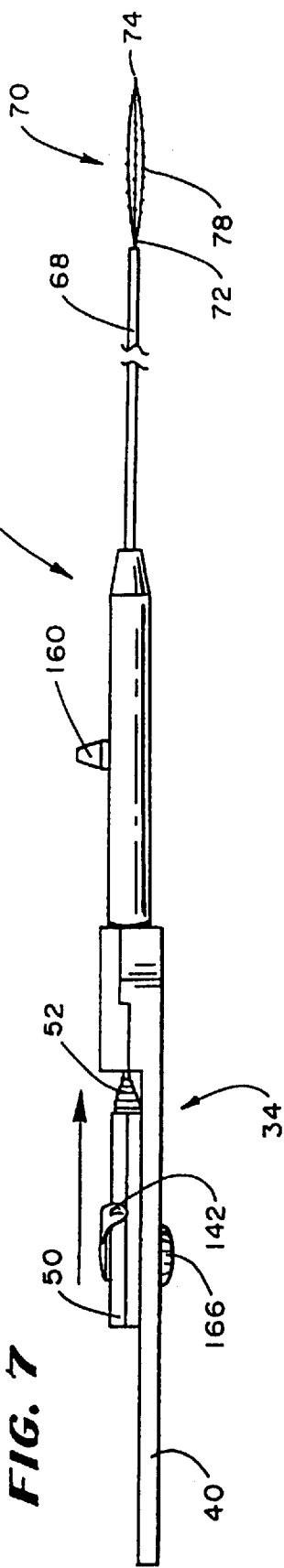

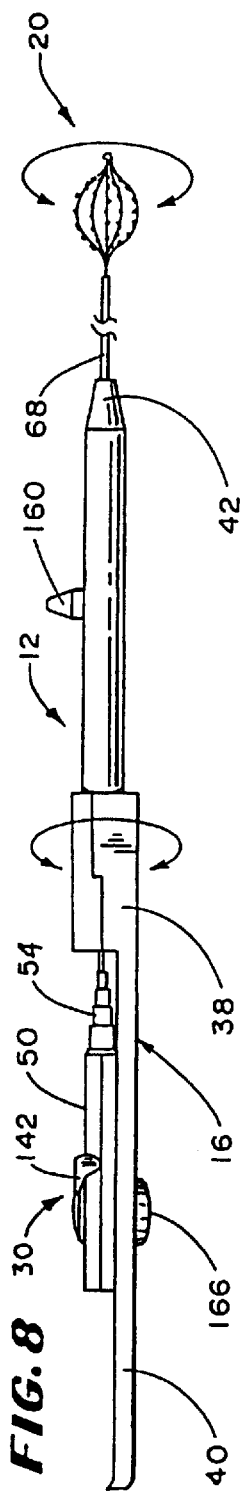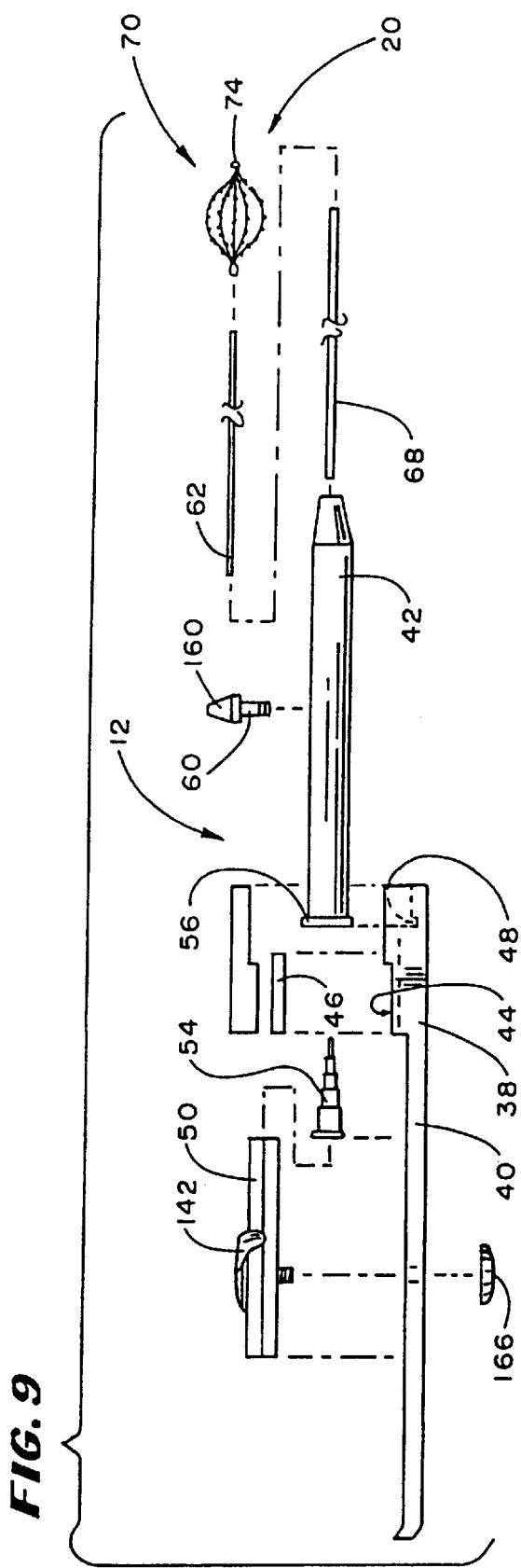

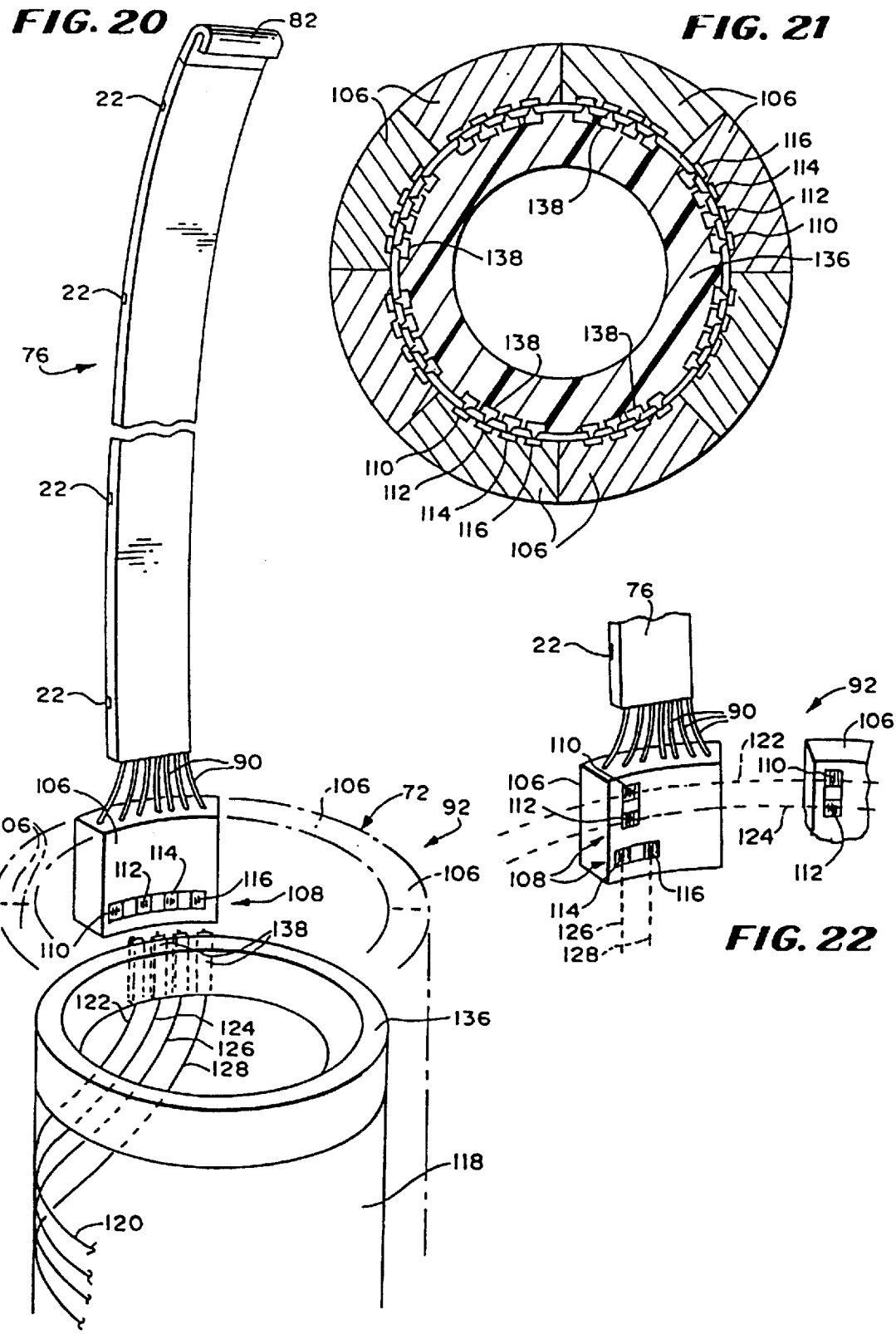

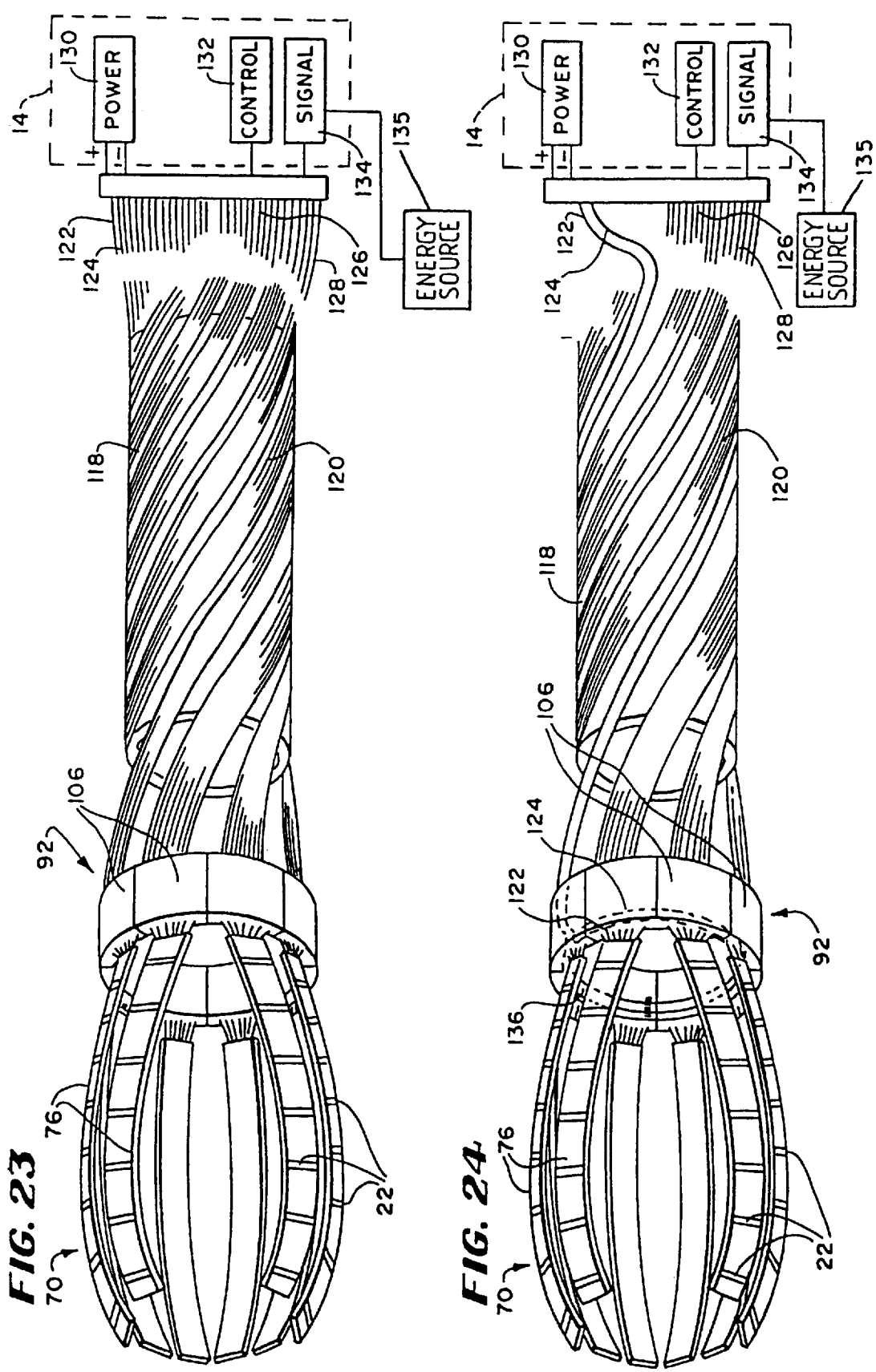

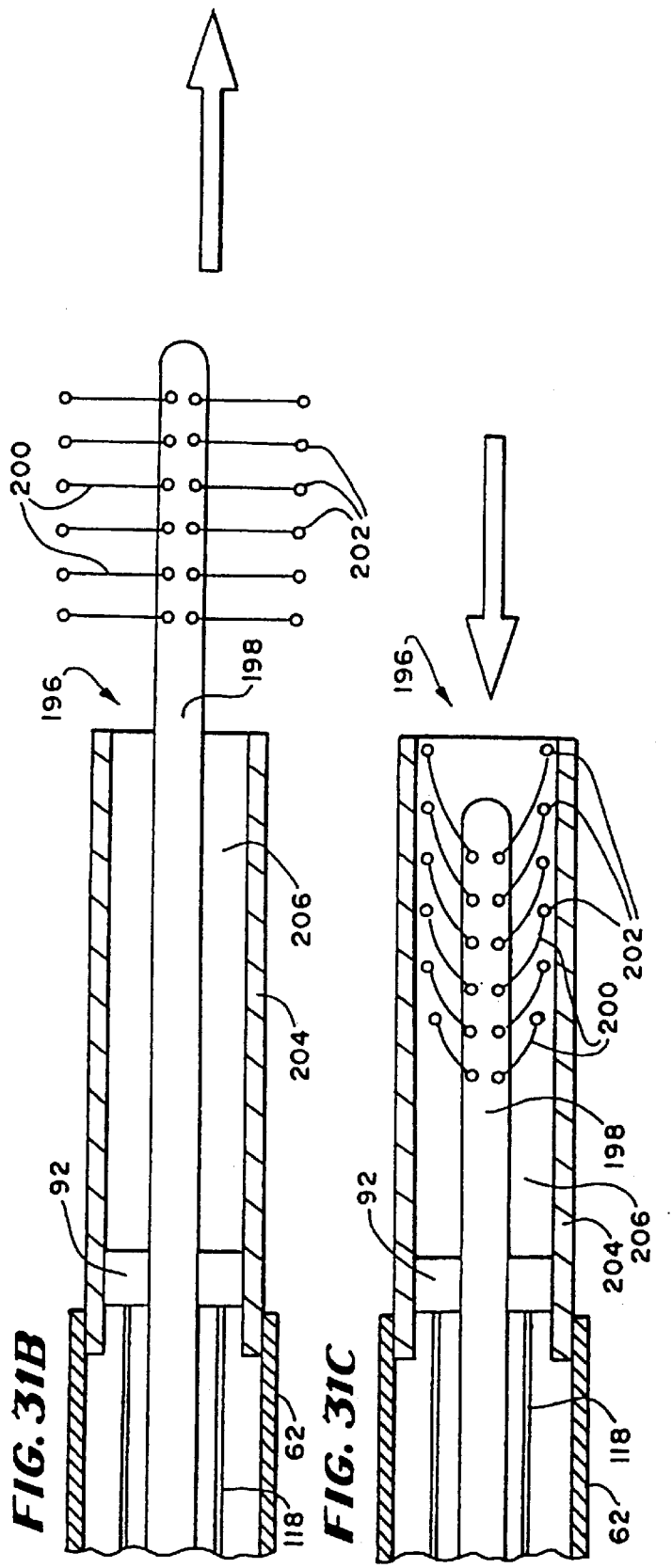

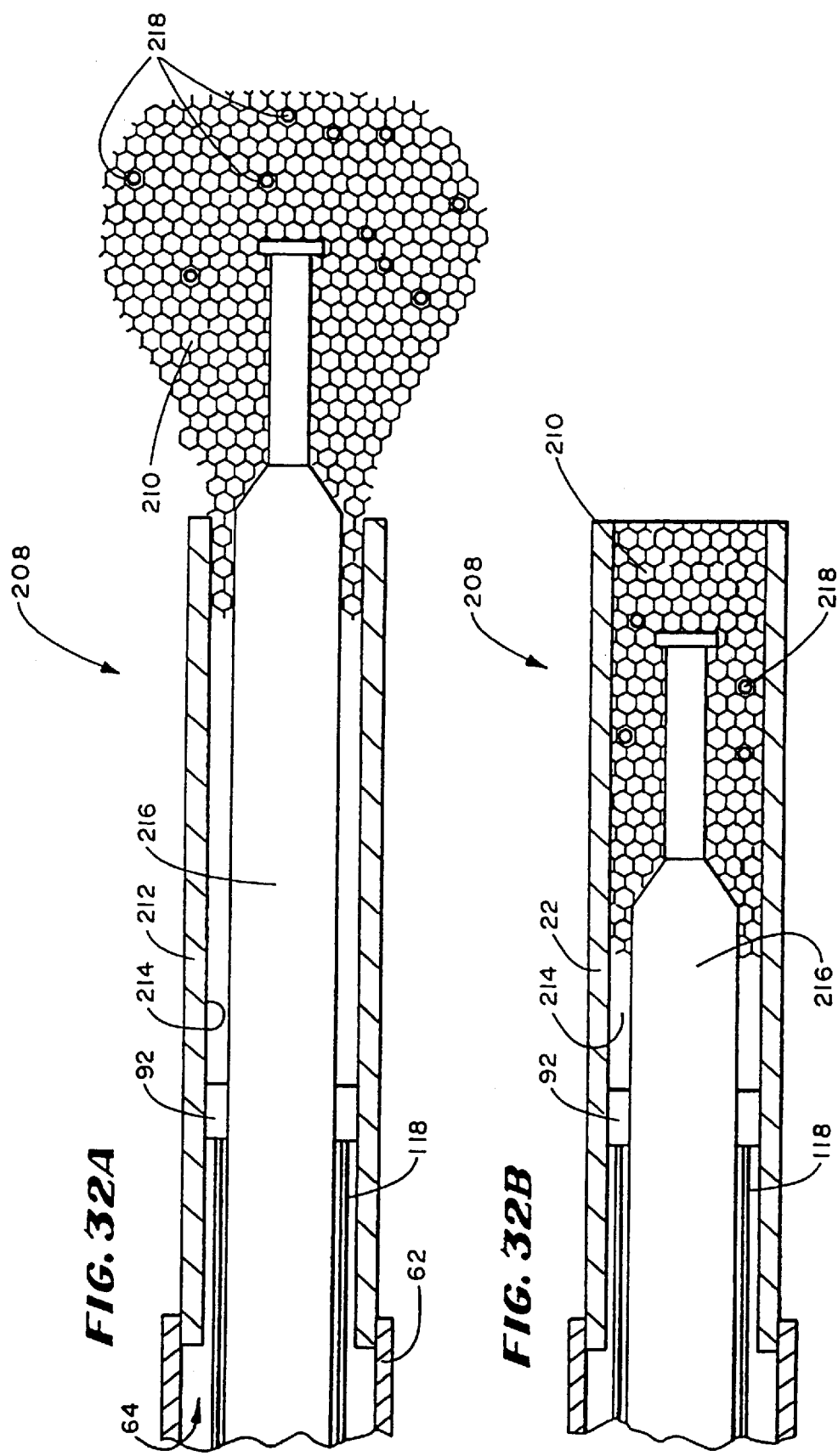

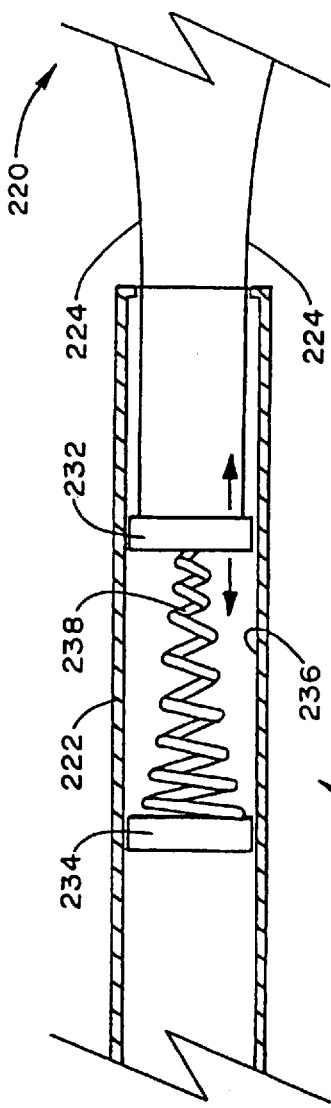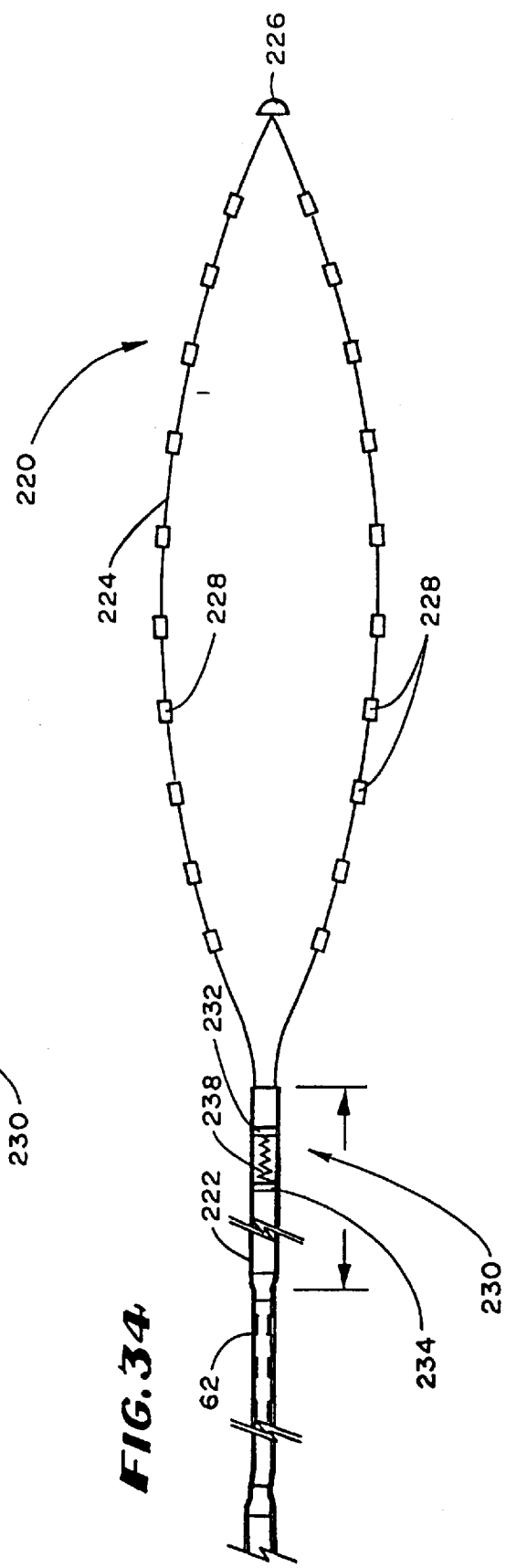
FIG.33
FIG.34

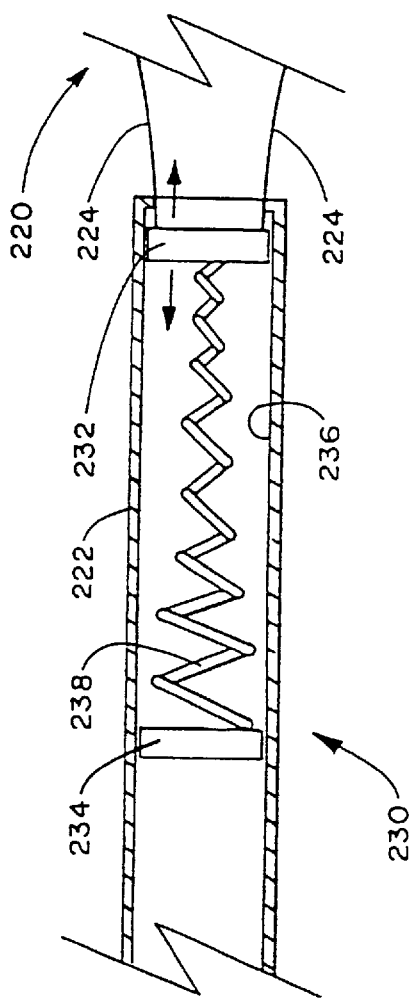
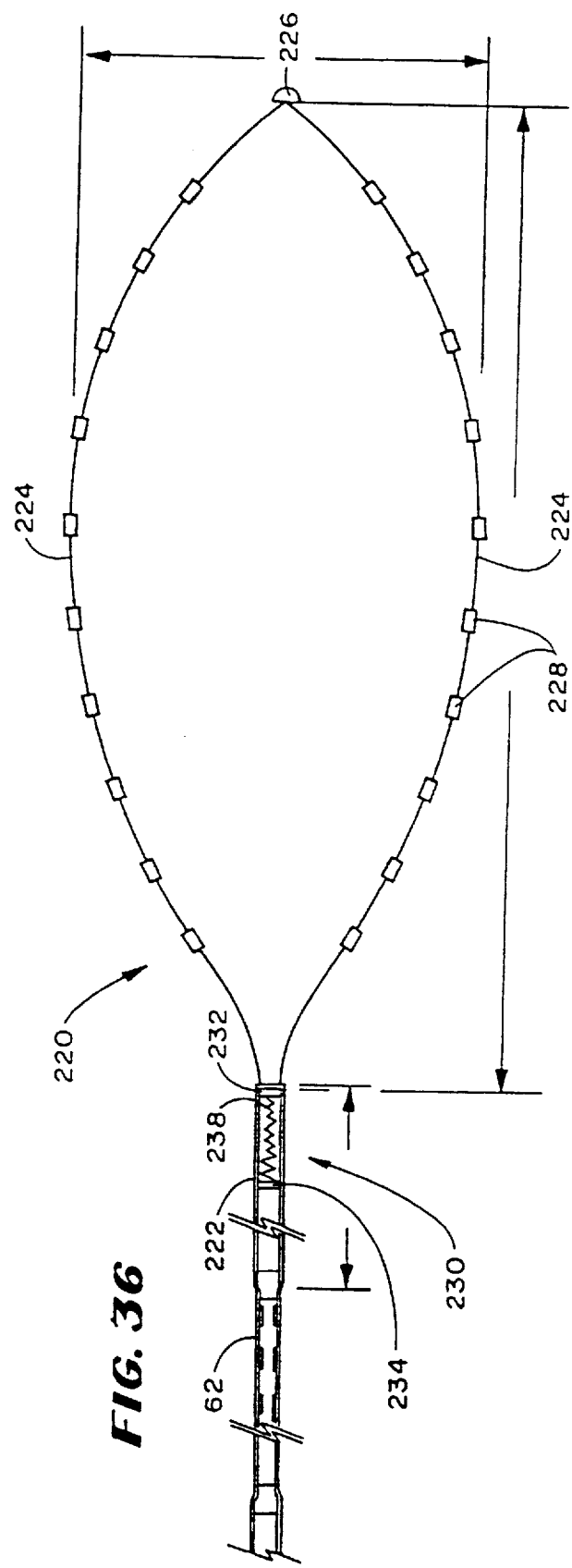
FIG. 35
FIG. 36

5,871,443

CARDIAC MAPPING AND ABLATION SYSTEMS

This is a divisional of application Ser. No. 08/636,174, filed Apr. 22, 1996, now abandoned, which is a divisional of application Ser. No. 08/168,476, filed Dec. 16, 1993, now U.S. Pat. No. 5,509,419, which is a divisional of application Ser. No. 07/951,157, filed Sep. 25, 1992, now U.S. Pat. No. 5,309,910.

FIELD OF THE INVENTION

The invention relates to percutaneous leads and related systems and methods for mapping the interior regions of the heart for diagnosis of cardiac conditions.

BACKGROUND OF THE INVENTION

Cardiac mapping is used to locate aberrant electrical pathways and currents emanating within the heart. The aberrant pathways cause the contractions of the heart muscle to take on peculiar and life threatening patterns or dysrhythmias.

Intracardiac mapping requires the careful positioning of an array of multiple electrodes within the heart. Various structures for these multiple electrode mapping arrays have been developed or proposed.

For example, Hess U.S. Pat. Nos. 4,573,473 and 4,690,148 and Desai U.S. Pat. No. 4,940,064 show the use of generally planar mapping arrays. Chilson U.S. Pat. No. 4,699,147 shows the use of a three dimensional basket mapping array. Gelinas U.S. Pat. No. 4,522,212 shows a spring apart array of electrode supporting fingers.

Regardless of the type of mapping array used, the physician is called upon to remotely move and manipulate the array within the heart in various ways. First, the physician must maneuver the array through a main vein or artery into a selected heart chamber. Then, the physician must locate the array at the desired endocardial location. Then, the physician must further move the array at the desire location to assure that all aberrant electrical pathways, if present, are located.

The development of prior mapping arrays has focused upon the requirements of mapping function itself. The prior development has overlooked the important need to continuously and variously move and manipulate the mapping array before, during, and after the mapping function.

SUMMARY OF THE INVENTION

An important aspect of the invention relates to providing a novel and improved construction for electrode carrying splines for improved cardiac mapping and ablation devices.

Briefly summarized the present invention provides an electrode assembly for use in interventricular cardiac mapping and probes formed thereby. The assemblies of the present invention involve the use of one or more elongated splines each of which carries a plurality of spaced apart electrodes thereon. Each spline has a means for attaching its proximal end to a supporting means, preferably the distal end of a flexible hollow tube located within the catheter. Each spline can further be provided with means to attach the distal end thereof to an end cap to form a mapping array or basket.

The body of each spline is formed of a plurality of alternating electrically conductive layers and the electrically non-conductive layers. A separate electrically conductive pathway is provided to connect each of the electrodes to a different one of the conductive layers. Each of the layers is electrically connected to an electrical signal processing device so that signals provided by each of the electrodes can be processed.

In accordance with one embodiment of the invention, the spline can be of a circular cross-section with each of the alternating conductive and non-conductive layers being in the form of concentric rings and each of the electrodes is in the form of a ring encircling the outer surface of the spline.

In accordance with a further embodiment of the invention, the electrode can be of an anisotropic rectangular cross-sectioned configuration. An array or basket formed of such splines provides a stable configuration resistant to twisting and thus insures accuracy and reliability of the cardiac mapping procedure.

BRIEF DESCRIPTION OF THE DRAWINGS

FIG. 2 is a top view of the probe associated with the system shown in FIG. 1, showing the operation of the steering mechanism;

FIGS. 3 and 4 are side elevation views of the probe associated with the system shown in FIG. 1, showing the operation of the deployment mechanism for the mapping array;

FIGS. 5 to 7 are side elevation views of the probe associated with the system shown in FIG. 1, showing the operation of the mechanism for opening and shaping the mapping array;

FIG. 8 is a side elevation view of the probe associated with the system shown in FIG. 1, showing the operation of the mechanism for rotating the mapping array;

FIG. 9 is an exploded side elevation view of the probe associated with the system shown in FIG. 1;

FIG. 20 is an enlarged perspective view, largely schematic, of the solid state circuit tube and one of eight microconnector chips associated with the mapping assembly shown in FIG. 1;

FIG. 21 is top view of the electrical attachment between microconnector chips and the solid state circuit tube shown in FIG. 20;

FIG. 22 is an enlarged perspective view, largely schematic, of an alternative embodiment for the solid state circuit tube and the microconnector chips associated with the mapping assembly shown in FIG. 1;

FIG. 23 is a schematic view of a power supply and signal control circuit for the microconnector shown in FIGS. 20 and 21;

FIG. 24 is a schematic view of an alternative power supply and signal control circuit for the microconnector shown in FIG. 22;

FIGS. 31A/B/C are side section views of an alternative deployable mapping assembly using a central spline with random electrode support filaments;

FIGS. 32A and B are side section views of an alternative deployable mapping assembly using a foam body;

FIG. 33 is a side section view of the base member of a dynamic mapping assembly that embodies the features of the invention shown in a contracted condition;

FIG. 34 is a side section view of the dynamic mapping assembly associated with the base member shown in FIG. 33 in a contacted condition;

FIG. 35 is a side section view of the base member of a dynamic mapping assembly that embodies the features of the invention shown in an expanded condition; and FIG. 36 is a side section view of the dynamic mapping assembly associated with the base member shown in FIG. 35 in an expanded condition.

DESCRIPTION OF THE PREFERRED EMBODIMENTS

Figure 1:
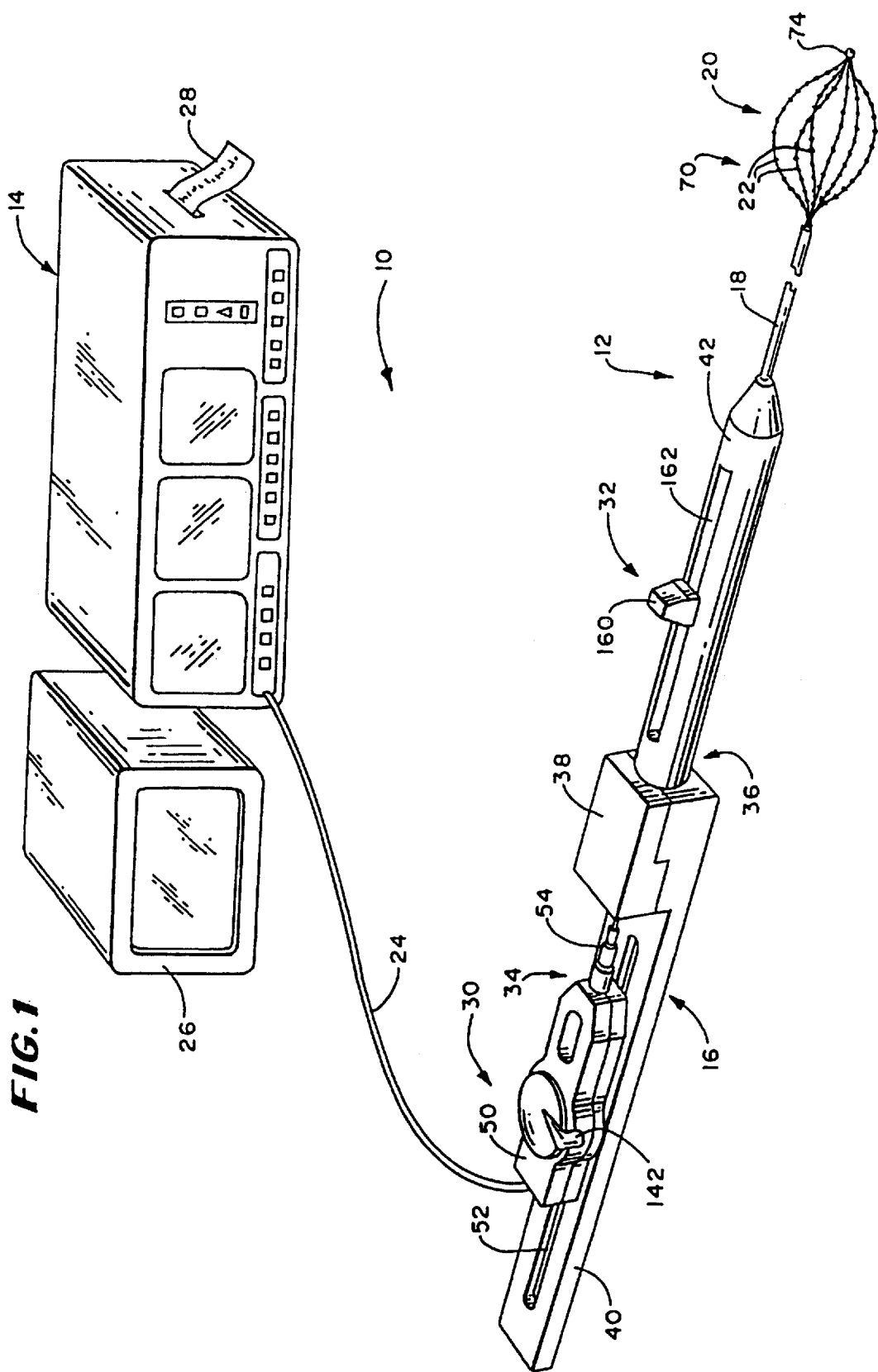
FIG. 1 is a perspective view of an endocardial mapping system that embodies the features of the invention.

FIG. 1 shows an endocardial mapping system 10 that embodies the features of the invention. The system 10 includes a hand-held probe 12 and an associated controller 14.

The probe 12 has a handle 16 and an attached flexible catheter 18. The catheter 18 slidably carries within an interior lumen a mapping assembly 20 that is extendable out of the distal end of the catheter.

The mapping assembly 20 establishes a three dimensional array of electrodes 22. In use, the mapping assembly 20 records the activation times, the distribution, and the waveforms of the electrical charges or potentials that trigger the pumping action of the heart muscle.

Leads 24 pass through the lumen of the catheter and connect the mapping assembly 20 to the controller 14. The controller 14 receives and processes the potentials recorded by the electrodes 22 on the mapping assembly 20. An attached CRT 26 visually presents the processed data for viewing by the attending physician. The controller 14 also has a printer 28 for presenting the processed data in strip chart form.

The physician positions the mapping assembly 20 by maneuvering the catheter 18 through a main vein or artery (which is typically the femoral artery) into a selected heart chamber. During this time, the mapping assembly 20 is carried in a compact, folded away position within distal end of the catheter 18 (as FIG. 3 shows). The physician can observe the progress of the distal catheter end using fluoroscopic or ultrasound imaging, or the like.

When the physician places the distal end of the catheter 18 in the desired endocardial location, he/she manipulates the control mechanisms of probe 12 to deploy and open the mapping assembly 20 into the desired three dimensional array 22 (as FIG. 1 shows).

The controller 14 analyses the signals received from the electrodes 22 to locate abnormal foci in the tissue that disrupt the normal heart rhythm and can cause cardiac arrhythmia. Once located, the physician can remove or destroy the abnormal foci by ablation to restore a normal heart rhythm. A separate RF or microwave ablation probe (not shown) can be used for this purpose. Alternatively, the mapping array 22 can itself include one or more ablating electrodes.

According to one aspect of the invention, the probe 12 includes four independent control mechanisms for the physician to manipulate in carrying out the multiple steps of the mapping procedure just generally outlined. The control mechanism are centrally located on the handle 16 to simplify error free manipulation of the catheter 18 and associated mapping assembly 20.

The first control mechanism 30 deflects the distal end of the catheter 18 (as FIG. 2 shows). This allows the physician to remotely point and steer the distal end of the catheter 18 within the body.

When the mapping assembly 20 is deployed, the first mechanism 30 can also be used to point and steer the mapping assembly 20 itself. This allows the physician to remotely maneuver the mapping assembly 20 into position against endocardial tissue.

The second mechanism 32 controls the deployment of the mapping assembly 20. The second mechanism 32 controls deployment of the mapping assembly 20 from a retracted position within the distal end of the catheter 18 (shown in FIG. 3) to an operating position outside the catheter 18 (shown in FIG. 4).

When retracted, the mapping assembly 20 occupies a low profile position that does not hinder the maneuvering within the body. When deployed in the operating position, the mapping assembly 20 can be opened to carry out its signal mapping function.

The third mechanism 34 opens the mapping assembly 20, when deployed. The third mechanism 34 moves the mapping assembly 20 between its completed closed, folded position (shown in FIG. 4) and an completely opened, unfolded position (shown in FIG. 5).

In the illustrated and preferred embodiment, the third mechanism 34 also controls the three dimensional shape of the mapping assembly 20. In this arrangement, the physician can remotely shape the mapping assembly 20 by manipulating the third mechanism 34.

In the illustrated embodiment, the third mechanism 34 progressively changes shape of the mapping assembly 20 from an elongated ellipse (as FIG. 7 shows), to an intermediate sphere (as FIG. 5 shows), to a toroid (as FIG. 6 shows). Using the third mechanism 34 for this purpose, the physician can alter the shape of the mapping assembly 20 to more closely match the particular endocardial profile to be recorded.

The fourth mechanism 36 controls the rotational position of the mapping assembly 20 independent of the rotational position of the catheter 18 (as FIG. 8 shows). In other words, the fourth mechanism 36 rotates the mapping assembly 20 without rotating the catheter 18.

Using the fourth mechanism 36, the physician can rotate the mapping assembly 20 within the heart, without otherwise rotating the catheter 18 within the access vein or artery.

The structural features of the catheter, the mapping assembly 20, and the associated control mechanism 30–36 can vary. These features will now be discussed in greater detail, as they appear in the illustrated embodiments.

1. The Probe Handle

Figure 10:
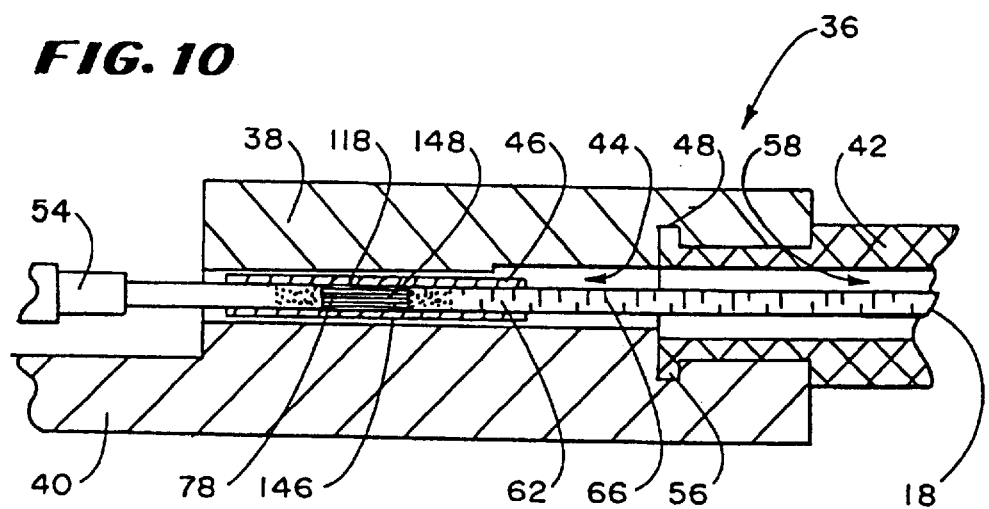
FIG. 10 is an enlarged side section view of the interior of the probe body shown in FIG. 9, when assembled, where the proximal end of the catheter joins the main probe body.
Figure 11:
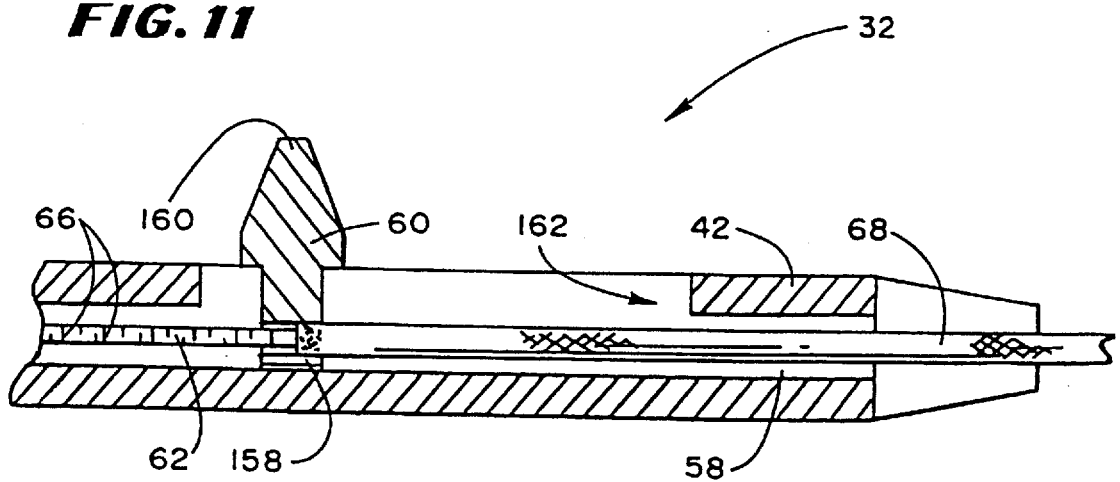
FIG. 11 is an enlarged side section view of the interior of the tip of the probe handle shown in FIG. 9, when assembled.

In the illustrated embodiment (as FIGS. 9 to 11 show), the probe handle 16 includes a main body 38, a base 40, and a tip 42. The handle 16 and its component parts can be constructed from various durable metal or plastic materials. In the illustrated embodiment, the handle 16 is mostly molded plastic.

The main body 38 has an interior channel 44 (see FIG. 10). A junction tube 46 is secured within the interior channel 44. The proximal end of the catheter 18 is, in turn, joined by adhesive or the like to the front end of the junction tube 46. As FIG. 10 also shows, the interior channel 44 also includes an annular groove 48 near its distal end, where the separately molded tip 42 is attached.

The handle base 40 is a premolded extension of the main body 38 (see FIG. 9). The base 40 is generally flat and carries a steering member 50. As will be described in greater detail later, the steering member 50 houses an actuator for the first control mechanism 30 to point and steer the distal end of the catheter 18.

The steering member 50 is also movable within a track 52 fore and aft upon the base 40 (see FIGS. 1 and 2 also). A telescopic shaft 54 connects the steering member 50 to the rear end of the junction tube 46. Fore and aft movement of the steering member 50 within the track 52 expands and collapses the telescopic shaft 54.

As will also be described in greater detail later, the fore and aft movement of the steering member 50 actuates the third control mechanism 34 to open and (in the preferred embodiment) shape the mapping assembly 20.

The handle tip 42 extends from the front of the main body 38. It includes a proximal flanged end 56 which seats within the annular groove 48 of the main body channel 44 (as FIGS. 9 and 10 show).

The flanged end 56 freely rotates within the annular groove 48. This allows the handle tip 42 to rotate relative to the main body 38. As will be described in greater detail later, the relative rotation between the handle tip 42 and main body 38 forms the basis for the fourth control mechanism 36.

As FIG. 10 shows, the handle tip 42 includes a center bore 58 that is axially aligned with the interior channel 44 of the main body 38. A carriage 60 moves within the center bore 58. As will be described in greater detail later, the movable carriage 60 actuates the second control mechanism 32 to control deployment the mapping assembly 20.

2. The Catheter

Figure 12:
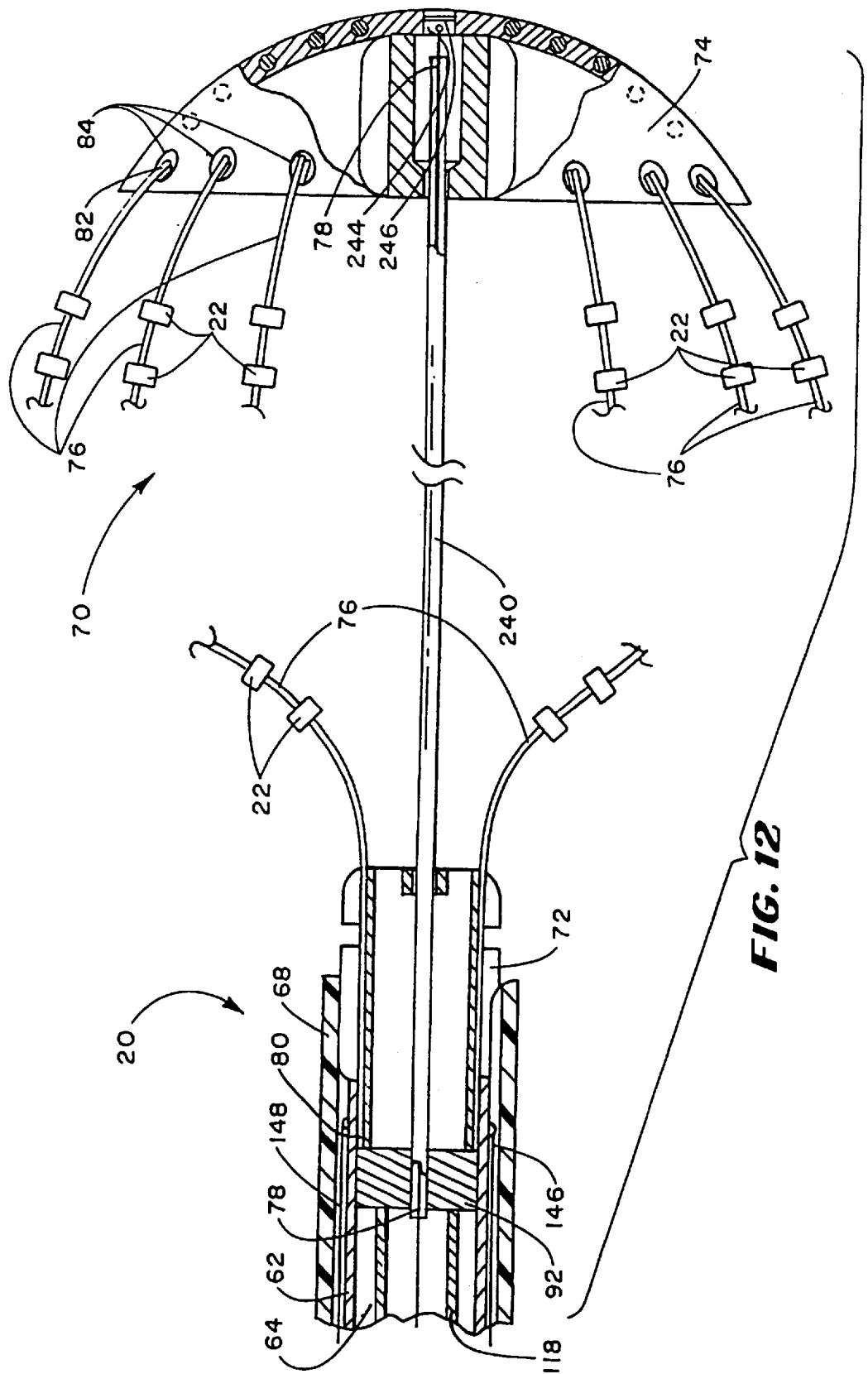
FIG. 12 is an enlarged side sectional view, with portions broken away, of the mapping basket associated with the system shown in FIG. 1.

The catheter 18 includes a flexible tube 62 having an interior bore or lumen 64 (see FIG. 12). The proximal end of the flexible tube 62 extends through the center tip bore 58 and into main body channel 44, where it is joined to the junction tube 46 (as FIG. 10 shows).

The flexible tube 62 may constructed in various ways. For example, it may comprises a length of stainless steel coiled into a flexible spring enclosing the interior bore 64.

In the illustrated and preferred embodiment, the tube 62 comprises a slotted, stainless steel tube. An array of slots 66 subtends the tube along its length. The slots 66 subtend less than one circumference of the shaft at an angle of between 270 to 300 degrees. The slots 66 are also preferably radially offset one from the other by about 30 to 120 degrees.

The slots 66 provide flexibility along the length of the tube 62. The pattern and arrangement of the slots 66 impart the necessary flexibility and torque transmission capabilities to tube 62.

Further details of the slotted tube 62 are disclosed in pending Lundquist U.S. patent application Ser. No. 07/657,106 filed Feb. 15, 1991 and entitled "Torquable Catheter and Method."

The catheter 18 also includes a sheath 68 enclosing the flexible tube 62. The sheath 68 is made from a plastic material, such as a polyolefin, polyurethane or polydimethylsiloxane. The sheath 68 has an inner diameter that is greater than the outer diameter of the tube 62. In this way, the sheath 68 slides along the outside of the tube 62 in response to the second control mechanism 32, to selectively enclose or expose the appended mapping assembly 20.

3. The Mapping Assembly

The mapping assembly 20 may take various different forms. In the embodiment illustrated in FIGS. 1 to 9, the mapping assembly 20 comprises a variably shaped basket 70, the details of which are best shown in FIG. 12.

The mapping basket 70 comprises a base member 72 attached to the distal end of the flexible catheter tube 62. The mapping basket 70 also includes an end cap 74. Generally flexible electrode supports or splines 76 extend in a circumferentially spaced relationship between the base member 72 and the end cap 74. The splines 76 carry the spaced sensing electrodes 22. Electrodes can also be located on end cap 74.

The outer diameters of the base member 72 and end cap 74 are less than the interior diameter of the movable sheath 68 (FIG. 12 shows this relationship with respect to the base member 72, but the end cap 74 is shown enlarged to better show the details of its construction). End cap 74 is preferably rounded or dome-shaped as shown. In this way, when moved toward the distal end of the flexible tube 62, the sheath 68 moves over and captures the mapping basket 70 (in the flattened position) and only the dome-shaped end of cap 74 is exposed. When moved the opposite way, the sheath 68 exposes the mapping basket 70 for use. In addition to electrodes located on splines 76A, one or more electrodes can also be located on end cap 74 to provide for additional signal measuring capability.

Still referring to FIG. 12, the mapping basket 70 further includes a generally stiff control wire 78. The distal end of the control wire 78 is attached to the end cap 74. From there, the control wire extends through the base member 72 and the bore 64 of the tube 62 for attachment to the third control mechanism 34, as will be described later.

Axial movement of the control wire 78 in response to actuation of the third control mechanism 34 moves the end cap 74 either toward or away from the base member 72. This flexes the splines 76 to vary the shape of the basket 70.

The splines 76 of the mapping basket 70 shown in FIG. 12 can assume various cross sectional shapes. The details of representative constructions will be discussed next.

A. The Basket Splines (i) Cylindrical Splines

Figure 13:
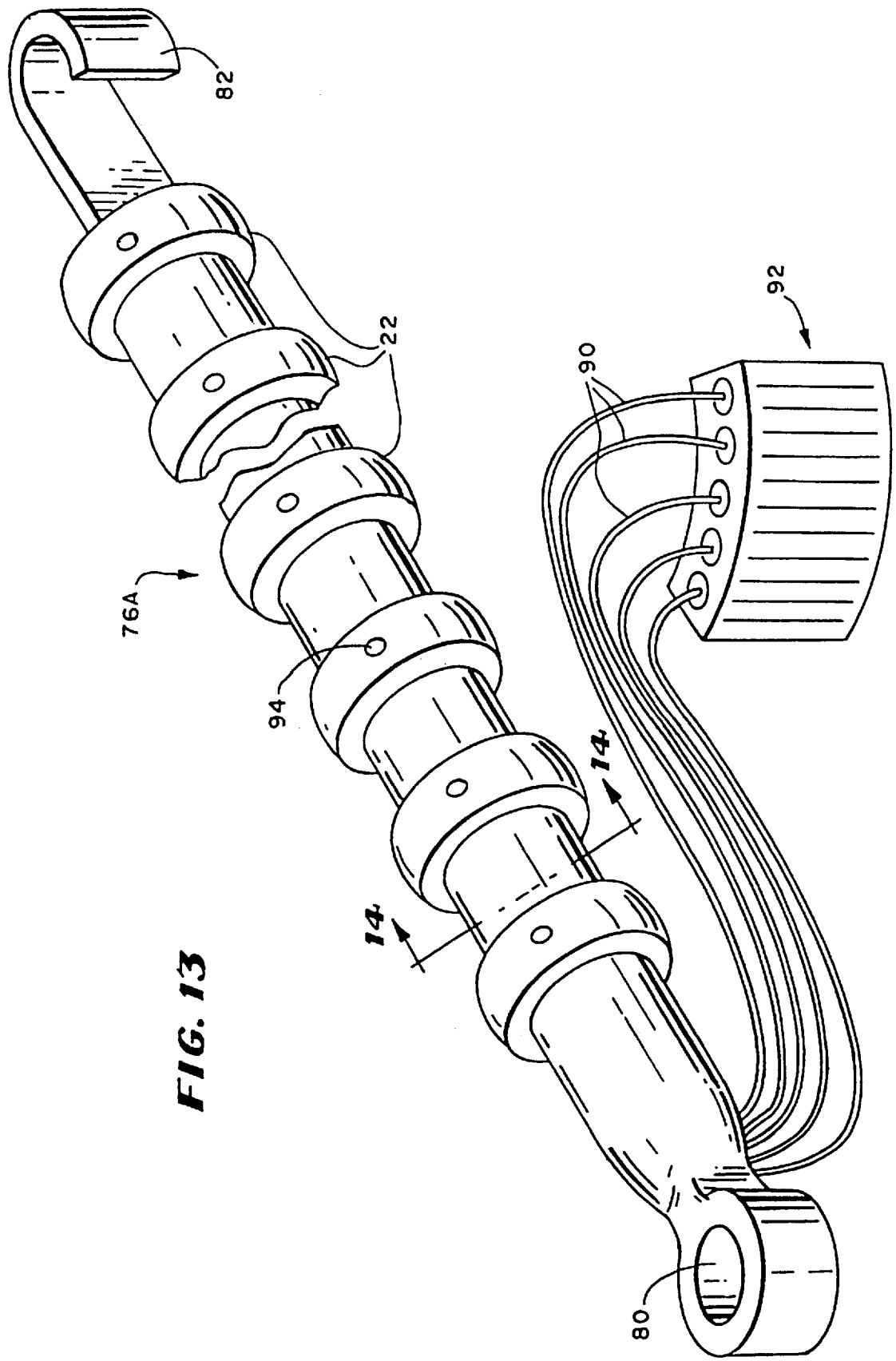
FIG. 13 is an enlarged perspective view, with portions broken away, of a cylindrical electrode support spline that the mapping basket shown in FIG. 12 can use.
Figure 14:
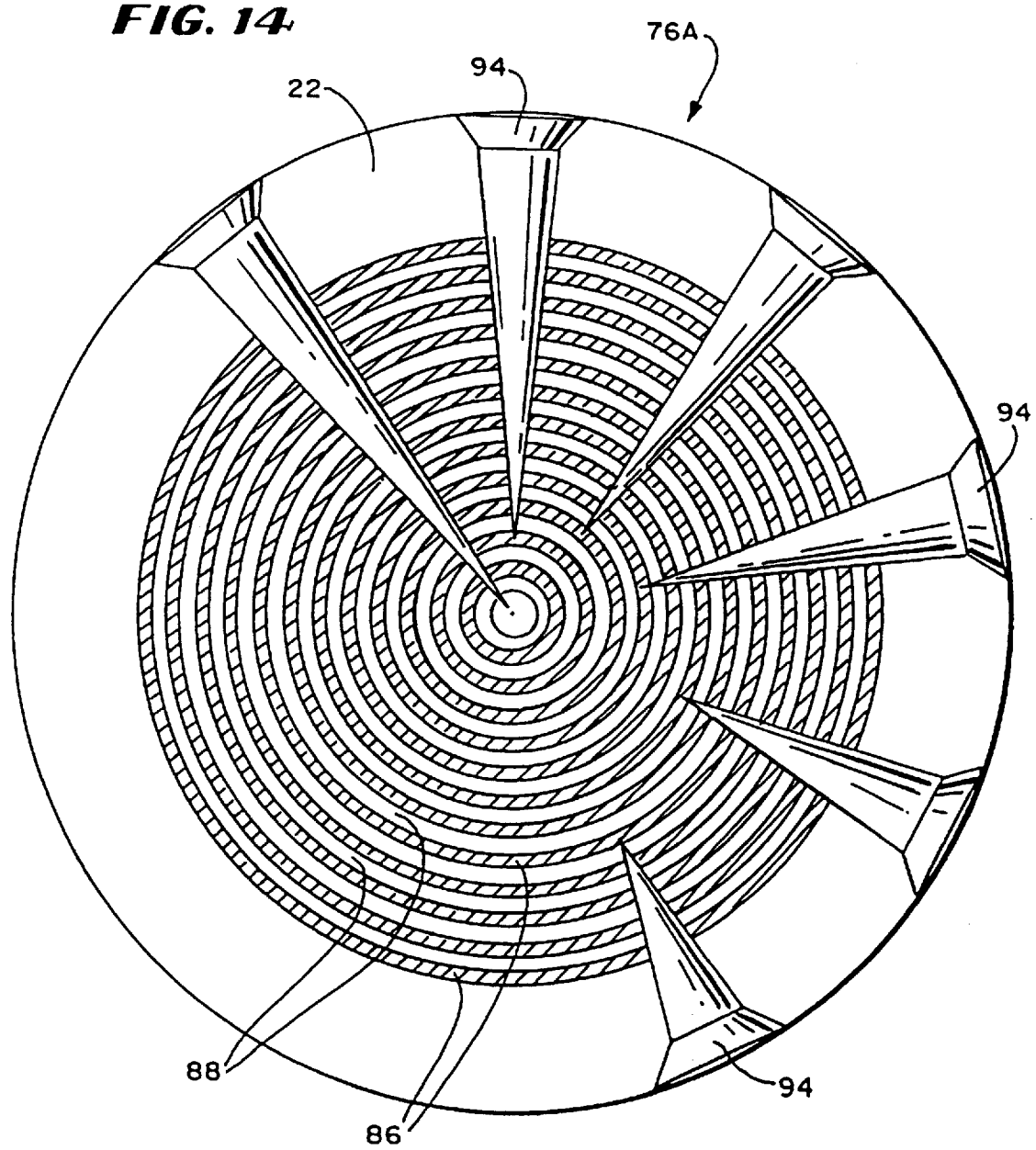
FIG. 14 is a greatly enlarged sectional view of the cylindrical electrode support spline taken generally along line 14—14 in FIG. 13.

FIGS. 13 and 14 show a spline 76A having a cylindrical cross section. The spline 76A carries the sensing electrodes 22 axially spaced along its length (six electrodes 22 are shown for the sake of illustration). The proximal end of the spline 76A includes an eyelet 80 for attachment to a pin on the base member 72. The distal end of the spline carries a hook 82 for quick connection to circumferentially spaced openings 84 on the end cap (as FIG. 12 shows). Of course, other quick connect coupling mechanisms can be used.

The cylindrical spline 76A can have an open interior passage for conducting individual signal wires connected to the sensing electrodes 22.

However, in the embodiment shown in FIGS. 13 and 14, the body of the cylindrical spline 76A is solid. It comprises multiple individual layers or substrates, as FIG. 14 shows. Alternating layers 86 are coated with an electrically conductive material, like platinum. Intermediate layers 88 of nonconductive material, like polyimide, separate the conductive layers 86.

The layers 86 and 88 can be applied, for example, by ion beam assisted deposition (IBAD), or similar vapor deposition techniques. In the illustrated embodiment, each layer is about 0.0005 inch to 0.002 inch thick.

As FIG. 13 shows, an individual signal wire 90 is attached to each conductive layer 86. The signal wires 90 exit the proximal end of the spline 76A and are joined to a microconnector 92, the details of which will be described in greater detail later.

The number of conductive layers 86 equals the maximum number of electrodes 22 that the spline 76A carries. In the illustrated embodiment, each cylindrical spline 76A carries a maximum of 12 sensing electrodes, so there are 12 conductive layers 86 and 12 signal wires (FIG. 13 shows only a portion of the electrodes 22 and the signal wires for the sake of illustration).

In the illustrated embodiment, each sensing electrode 22 comprises a flexible substrate such as a silicone rubber body that has been coated by IBAD with platinum. Each sensing electrode is slipped into position over the spline 76A and there fastened by adhesive or the like. Alternatively, the rubber bodies can be molded in place over the spline and subsequently coated with a conductive layer by IBAD.

A wire or pin 94 made of electrical conductive material (such as platinum) is inserted through each electrode 22 and into the body of the spline 76A. Each pin 94 is coated with an insulating material, except for its head end and its tip end.

As FIG. 14 shows, the pins 94 have different prescribed lengths, so that their tip ends reach different conductive layers 86. Each pin 94 individually conducts the signals received by its associated sensing electrode 22 to one conductive layer 86. In this way, the signals sensed by each electrode 22 is transmitted by a different conductive layer 86 to the associated signal wire 90.

(ii) Rectilinear Splines

Figure 15:
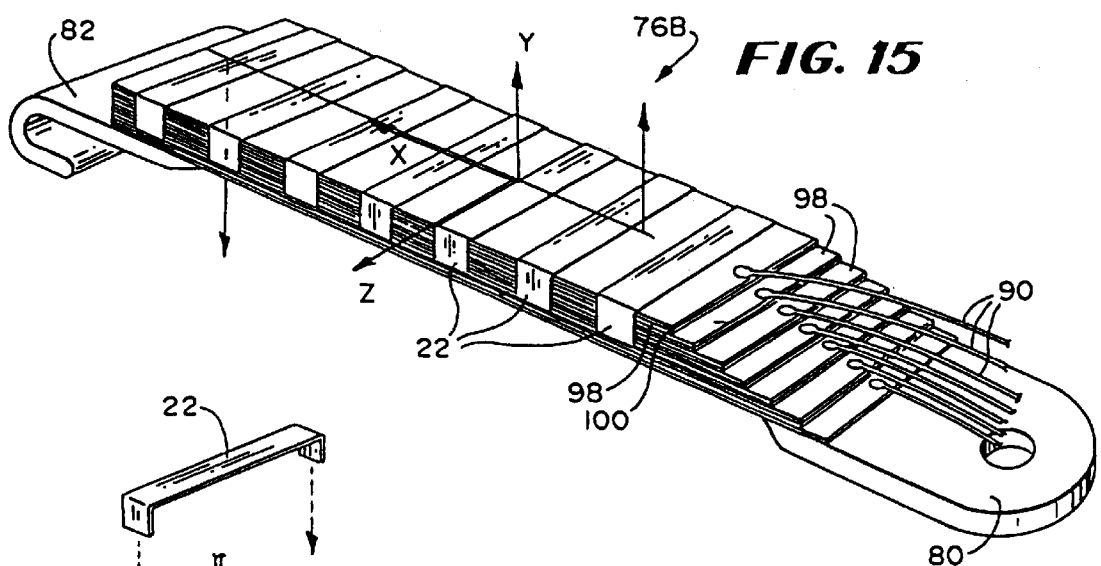
FIG. 15 is an enlarged perspective view of a rectilinear spline that the mapping basket shown in FIG. 12 can use.

FIG. 15 shows an electrode support spline 76B having a general flat, rectilinear cross section.

Unlike the cylindrical spline 76A shown in FIG. 13, the rectilinear spline 76B has anisotropic stiffness. It exhibits the flexibility to deflect or bend in one plane along its longitudinal X axis 96 (in the direction of the Y axis as shown by arrows in FIG. 15). However, it exhibits stiffness to resist flexing or twisting about its longitudinal X axis 96 in the direction of the Z axis.

As FIG. 15 shows, each rectilinear spline 76B carries sensing electrodes 22 axially spaced along its longitudinal axis 96. Like the cylindrical spline 76A, the proximal end of the rectilinear spline 76B includes an eyelet 80 for attachment to the basket base member 72. The distal end of the spline 76B carries a hook 82 for quick connection to the circumferentially spaced openings 84 on the basket end cap 74 (see FIG. 12).

When so connected, the anisotropic stiffness of each rectilinear spline 76B resists twisting about its longitudinal axis 96. This keeps the basket 70 torsionally rigid. The adjacent splines 76B are retained in the desired circumferentially spaced relationship.

Still, axial movement of the control wire 78 will flex each of the rectilinear splines 76B centrally outwardly along their longitudinal axes 96 in the direction of their Y axes. This will alter the circumferential shape of the basket 70 (as FIGS. 5 to 7 show).

Due to their anisotropic stiffness, adjacent splines 76B will resist twisting. The assembled basket 70 will therefore also resist twisting and will retain a desired symmetrical three dimensional shape about its longitudinal axis.

Figure 18:
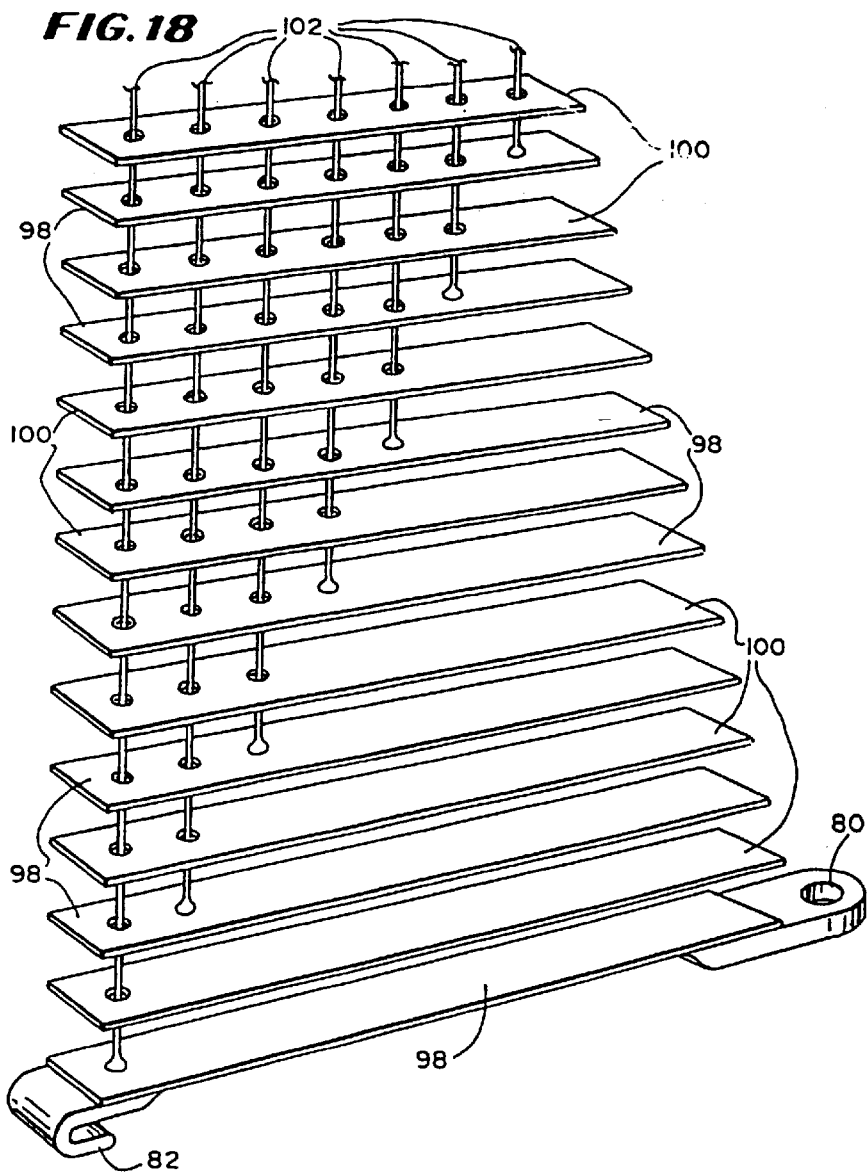
FIG. 18 is an exploded perspective view of the rectilinear spline shown in FIG. 15, showing its multiple conductive and nonconductive layers.
Figure 19:
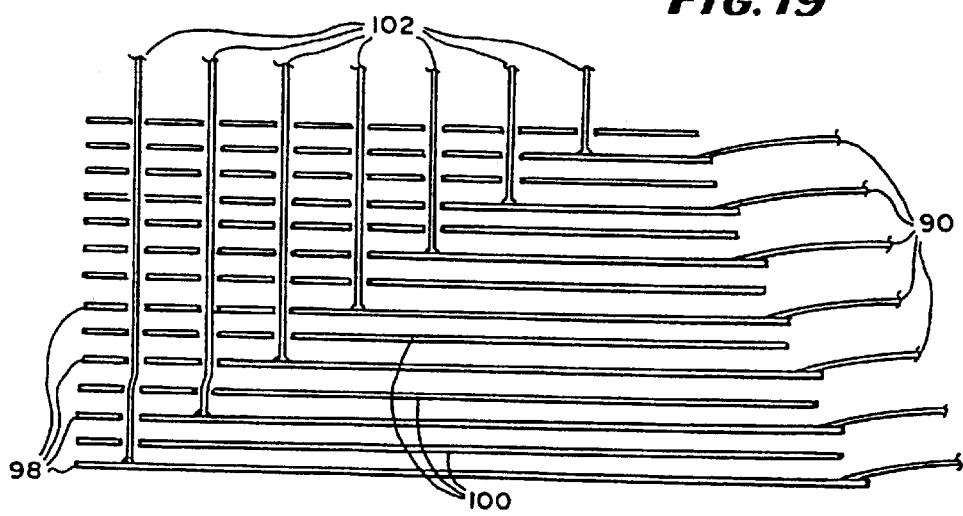
FIG. 19 is a schematic exploded side view of the multiple conductive and nonconductive layers of the rectilinear spline shown in FIG. 18.

In the embodiment shown in FIG. 15, the spline 76B comprises multiple conductive layers 98 separated by intermediate nonconductive layers 100 (as FIGS. 18 and 19 best show). The conductive layers 98 are coated with an electrically conductive material, such as platinum. The conductive layers are preferably 0.005 to 0.002 inch in thickness. The nonconductive layers 100 are made of a nonconductive material, such as a polyimide or similar polymeric material.

Figure 16:
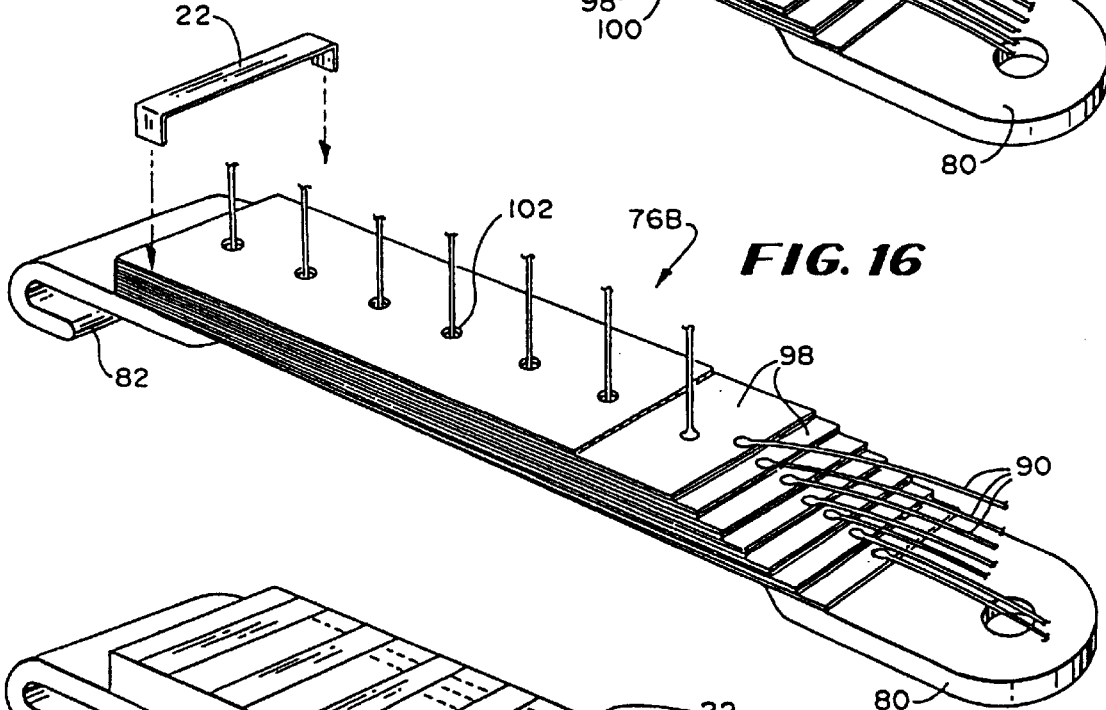
FIG. 16 is a perspective view of the rectilinear spline shown in FIG. 15 before attachment of the electrodes.

As FIGS. 18 and 19 show, an electrode wire 102 is soldered to each conductive layer 98. The individual electrode wire 102 for one conductive layer 98 is axially spaced apart from the electrode wire 102 for the next conductive layer 98. As FIGS. 18 and 19 also show, the electrode wires 102 from the lower conductive layers 98 pass through plated through openings 102 in successive upper conductive and nonconductive layers 98 and 100 to exit the top surface of the spline 76B (as FIG. 16 also shows). There, an electrode 22 is soldered to each electrode wire 102.

As FIGS. 15; 16; 18; and 19 show, the proximal ends of the various conductive and nonconductive layers 98 and 100 are preferably arranged in stepwise fashion. This exposes each conductive layer 98 to facilitate connection of the signal wires 90 by soldering.

Figure 17:
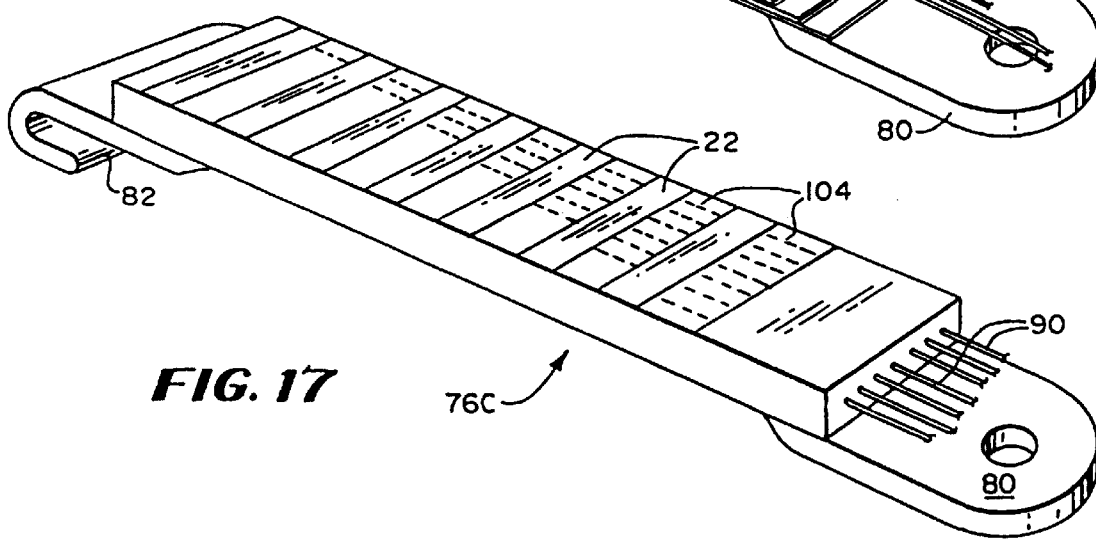
FIG. 17 is an enlarged perspective view of an alternative embodiment of a rectilinear spline that the mapping basket shown in FIG. 12 can use.

In an alternative arrangement (as FIG. 17), the electrodes 22 are vapor deposited on the surface of the rectilinear spline 76C. In this arrangement, the surface of the spline 76C also carries a solid state printed circuit 104 formed by either ion deposition or etching. The circuit 104 conducts signals from the individual electrodes 22 to individual signal wires 90 attached at the proximal end of the spline 76C. An eyelet 80 and a hook 82 provide for quick attachment of the spline 76C between the basket base member 72 and end cap 74, as previously described.

B. The Microconnector

The multiple signal wires 90 leading from the sensing electrodes can be bundled together and passed as individual wires through the bore 64 of the flexible guide tube 62 for attachment to the controller 14. Laser welding can be used to minimize the cross sectional area of the electrical connections.

In the illustrated and preferred embodiment, the number of electrically conductive wire leads passing through lumen 64 is minimized by using solid state microconnector 92 in the base member 72 (see FIG. 12). FIGS. 20 to 24 show the details of the microconnector 92.

As FIG. 20 shows, the microconnector 92 includes one microprocessor chip 106 for each electrode support spline 76 in the basket 70. FIGS. 20 to 24 assume an array of 56 sensing electrodes 22 on the basket 70. One or more of the sensing electrodes can also serve as ablation electrodes, as well.

In this array, there are eight splines 76, with each spline 76 holding seven sensing electrodes 22. In this arrangement, the microconnector 92 includes eight individual chips 106 (as FIG. 21 shows), with seven electrode signal wires 90 attached to each chip 106 (as FIG. 20 shows).

The chips 106 serve as switches controlled by the controller 14. Each chip 106 receives seven individual signals, one from each electrode 22 on the associated spline 76. Each chip 106 transmits only a selected one of the electrode signals at a time to the controller 14, subject to the switching signals that the controller 14 generates. The switching signals of the controller 14 thereby multiplex the electrode signals through the microconnector 92. This reduces the number of electrical pathways required through lumen 64.

As FIG. 20 also shows, each chip 106 includes an I/O buss 108 comprising a power (+) contact 110 and a power (−) contact 112. The power contacts 110 and 112 receive power from a supply 130 within the controller 14. The I/O buss 108 also includes an input switching (or control) contact 114, which receives the switching signals from the signal generator 132 within the controller 14 to select the input signal wire to be sampled. The control contact 114 can also receive ablation energy through the signal generator 134 from a source 135, to thereby use one or more of the associated sensing electrodes for tissue ablation.

The I/O buss 108 further includes an output signal contact 116 for transmitting the selected electrode signal to the signal processor 134 within the controller 14. FIGS. 23 and 24 diagrammatically show the components 130; 132; and 134 of the controller 14.

The power, control, and output signals of each chip 106 are transmitted to and from the buss 108 along an electrical conduction conduit 118 carried within the lumen 64 of tube 62. The electrical conduit 118 can be variously constructed. It can, for example, comprise coaxial cable.

In the illustrated embodiment (see FIG. 21), the conduit 118 comprises a mylar tube. The surface of the tube 118 carries a solid state printed circuit 120 formed by either ion deposition or etching.

The specific configuration of the circuit 120 deposited on the tubular conduit 118 can vary. In the embodiment shown in FIG. 23, the circuit 120 comprises 32 individual conducting paths that extend in a helical array deposited about the axis of the tube. As FIG. 20 also shows, the array includes one power (+) line 122 and one power (−) line 124 for each chip 106 (for a total of 16 power (+) and (−) lines). These lines are connected to the power supply 130 within the controller 14.

The array shown in FIGS. 20 and 23 also includes one input control line 126 and one signal output line 128 for each chip 106 (for 16 additional lines, comprising a total of 32 conducting lines). These lines 126 and 128 are connected, respectively, to the signal multiplexing control circuit 132 and to the signal processing circuit 134 of the controller 14.

As FIG. 20 and 21 show, a stainless steel ferrule 136 electrically interconnects the lines of the circuit 120 with the microconnector 92. The ferrule is located within the distal end of the mylar tube 118. The ferrule 136 has a prescribed array of 32 cone points 138. The cone points 138 electrically interconnect the appropriate power (+) and (−) lines 122 and 124, the control input line 126, and the signal output line 128 to the associated contacts 110/112/114/116 of the I/O buss 108 of each chip 106.

In an alternative arrangement (as FIGS. 22 and 24 show), the circuit 120 carried on the tube 118 is reduced to 18 lines. This circuit 120 also extends in a helical array deposited about the axis of the tube 118. This array carries only one power (+) line 122 and one power (−) line 124, connected to the power supply 130. As FIG. 24 shows, the distal ends of the power (+) line 122 and the power (−) line 124 encircle the distal end of the tube 118 in axially spaced loops.

In the particular array shown in FIG. 24, the loop of the power (+) line 122 is located closer to the distal end of the tube 118 than the loop of the power (−) line 124 (see FIG. 22, also).

The array carried by the tube 118 also includes one input control line 126 and one signal output line 128 for each chip 106, for a total of 16 additional lines. As before described, these lines 126 and 128 are connected to the multiplexing and signal analyzing circuits 132 and 134 of the controller 14 (as FIG. 24 shows). As FIG. 22 shows, the lines 126 and 128 terminate on the distal end of the tube 118 below the power (+) and power (−) loops 122 and 124 just described.

In this arrangement (as FIG. 22 shows), a portion of the I/O buss 108 of each chip 106 is arranged circumferentially. The top two contacts 110 and 112 comprise the power (+) and power (−) contacts, respectively. These are commonly connected by cone points 138 on the ferrule 136 to the power (+) and power (−) loops 122 and 124, as FIG. 22 shows.

The bottom two contacts 114 and 116 of the I/O buss 108 comprise the control input and signal out leads. These contacts 114 and 116 are circumferentially arranged below the axial power contacts 110 and 112. The cone points 138 on the ferrule 136 appropriately connect the control input line 126 and the signal output line 128 to these circumferentially arranged contacts 114 and 116 of the I/O buss 108, as FIG. 22 shows.

4. The Probe Control Mechanisms

A. The Steering Control Mechanism

Figure 25:
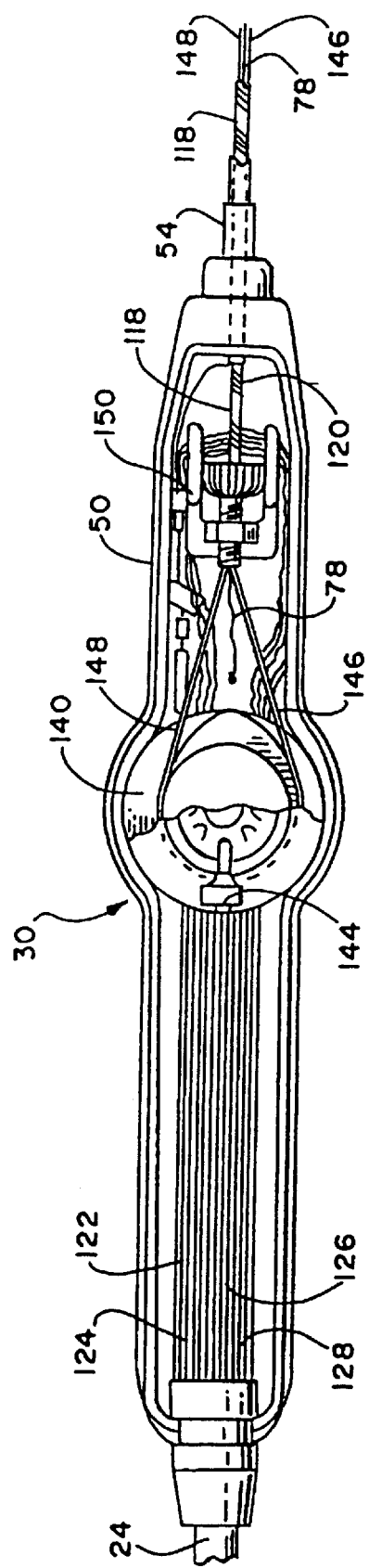
FIG. 25 is a top view of the interior of the steering mechanism associated with the probe shown in FIG. 1.

In the illustrated arrangement shown in FIG. 1, the first probe control mechanism 30 occupies the interior of the steering member 50. FIG. 25 shows further details of this construction.

The first mechanism 30 includes a rotating cam wheel 140 housed within the steering member 50. A lever 142 on the exterior of the steering member 50 (see FIG. 1) is attached to the interior cam wheel 140. Movement of the steering lever 142 by the user rotates the cam wheel 140.

As FIG. 25 shows, the cam wheel 140 carries a fastener 144 between its right and left side surfaces. Fastener 144 holds the proximal ends of right and left probe steering wires 146 and 148, which are soldered to the interior of the fastener 144.

The steering wires 146 and 148 extend from the opposite ends of the fastener 144 and along the associated right and left sides of the cam wheel 140. The steering wires 146 and 148 exit the front of the steering member 50 through the interior bore of a tension screw assembly 150, passing through the telescopic shaft 54 and into the junction tube 46, as FIG. 10 shows.

The steering wires 146 and 148 extend further along within the flexible shaft bore 64. Near the distal end of the tube 62, the steering wires 146 and 148 pass outside the bore 64 through exit holes (not shown). As FIG. 12 shows, solder connects the end of the left steering wire 148 to the left side of the distal end of the flexible tube 62. Likewise, solder connects the end of the right steering wire 146 to the right side of the distal end of the flexible tube 62.

Left rotation of the cam wheel 140 pulls the left steering wire 148 to bend the distal end of the tube 62 to the left. Likewise, right rotation of the cam wheel 140 pulls the right steering wire 146 to bend the distal end of the tube 62 to the right.

In this way, the first control mechanism 30 steers the distal end of the flexible tube 62 and, with it, the attached mapping basket 70 (as FIG. 2 shows).

Figure 26:
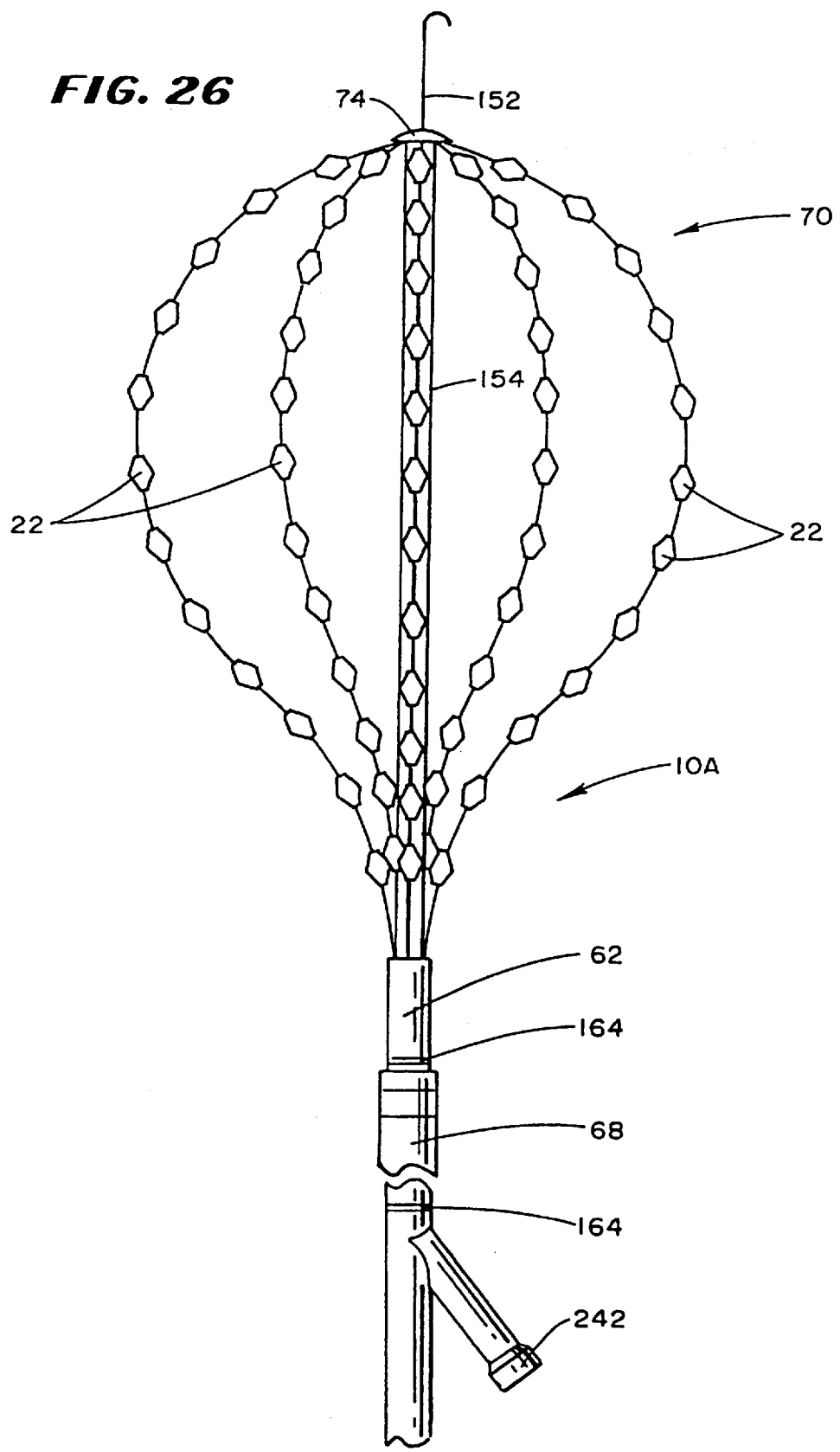
FIG. 26 is a view of the distal end of an alternative catheter having a mapping assembly that is located using a guide wire, instead of a steering mechanism.
Figure 27:
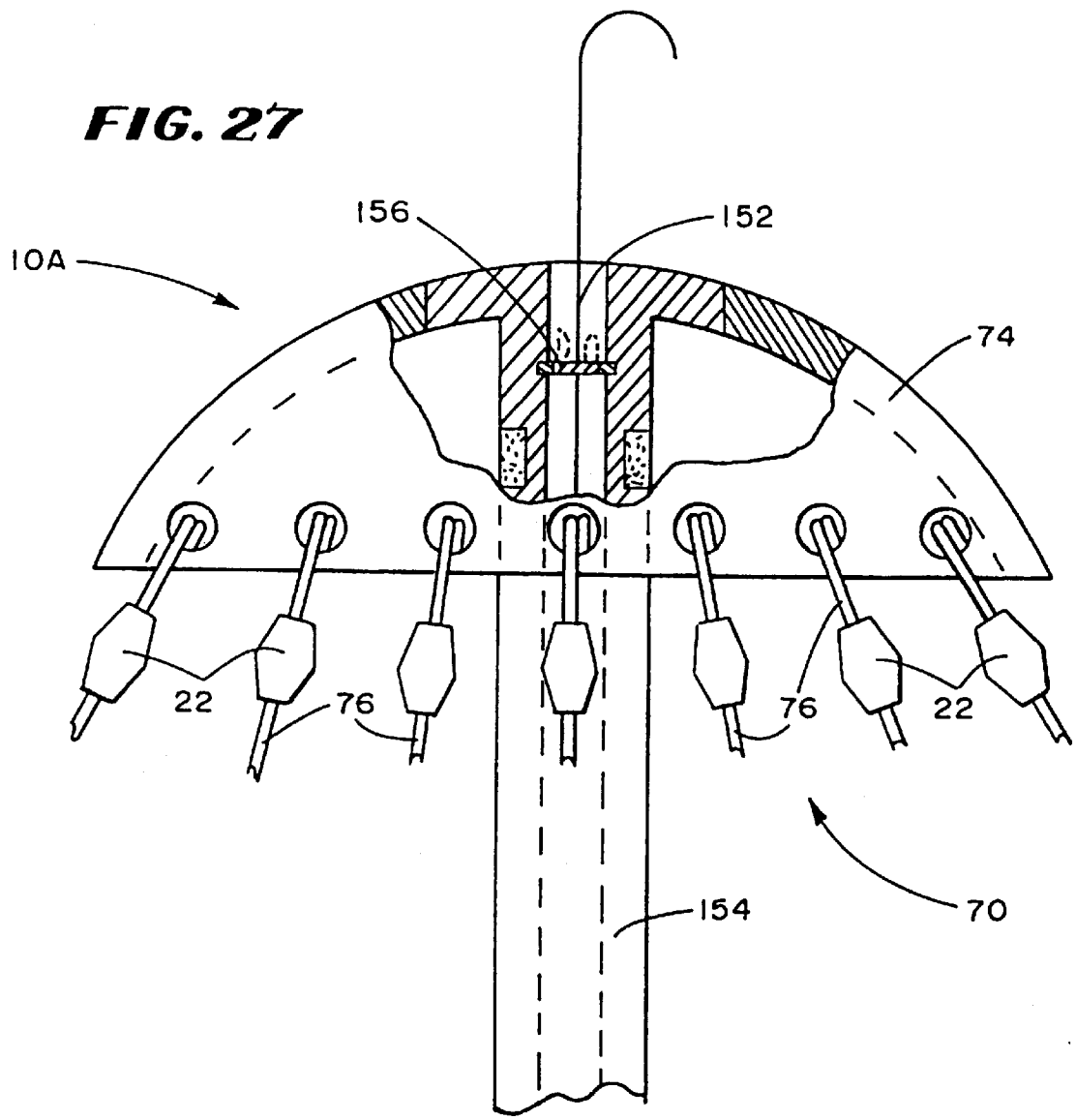
FIG. 27 is an enlarged view of the end cap of the mapping assembly shown in FIG. 26.

It should be appreciated that, instead of using an active onboard mechanism for steering the flexible tube 62, a wire can be used to guide and position the distal end of the tube 62 in the heart. FIGS. 26 and 27 show this alternative, over-the-wire embodiment, which lacks an onboard steering mechanism.

In the embodiment shown in FIGS. 26 and 27, the probe 10A includes an interior guide wire 152. The guide wire 152 extends from the handle (not shown), through the bore 64 of the flexible tube 62, passing through a central guide tube 154 in the mapping basket 70.

In use, the physician first maneuvers the guide wire 152 through the main vein or artery into a selected heart chamber. Then, the physician passes the tube 62 of the probe 10A with the attached mapping basket 70 over the guide wire 152 into position.

In this embodiment (as FIG. 26 shows), the probe 10A still preferably includes a slidable sheath 68 for temporarily enclosing the mapping basket 70 while being guided over the wire 152 into position (as FIGS. 3 and 4 show).

As FIG. 27 shows, the over-the-wire probe 10A also preferably includes a one-way annular valve 156 in the guide tube 154. The valve 156 prevents the back flow of blood and other fluids within the heart chamber into the guide tube 154 and the interior regions of the probe 10A.

B. The Mapping Assembly Deployment Mechanism

In the illustrated arrangement, the second mechanism 32 occupies the tip 42 of the probe handle 16. FIG. 11 shows further details of this construction.

As FIG. 11 shows, the second mechanism 32 includes a carriage 60 that moves within the center bore 58 of the handle tip. The carriage 60 includes an opening 158 concentric with the axis of the center bore 58, through which the flexible tube 62 passes. As FIG. 11 shows, the outer diameter of the flexible tube 62 is less than the inner diameter of the carriage opening 158.

The carriage member 60 has an exposed actuator 160 that extends through an elongated slot 162 in the handle tip (as FIGS. 1 and 2 also show). The slot 162 extends along the axis of the center bore 58. Fore and aft movement of the actuator 160 by the user moves the carriage member 60 within the center bore 58 axially over the flexible tube 62.

As FIG. 11 further shows, the proximal end of the sliding sheath 68 is fastened by adhesive or the like to the carriage 60. Carriage movement as just described will thus also slide the attached sheath 68 axially over the flexible tube 62.

When the actuator 160 occupies the fully forward position in the slot 162 on the handle tip 42 (as FIG. 3 shows), the distal end of the sheath 68 is generally coterminous with the end cap 74 of the mapping basket 70. The distal end of the sheath 68 will thereby enclose the entire mapping basket 70 in a closed, collapsed condition.

When the physician subsequently moves the actuator 160 to the fully rearward position in the slot 162 on the handle tip 42 (as FIG. 4 shows), the distal end of the sheath 68 is generally coterminous with the base member 72 of the mapping basket 70. This exposes the mapping basket 70 for use. In this way, the second mechanism 32 is used to deploy and retract the mapping basket 70.

Preferably (as FIG. 26 best shows), the distal end of the flexible tube 62 includes one or more O-rings or gaskets 164. The gaskets form a fluid tight seal between the flexible tube 62 and sliding sheath 68 to prevent the back flow of blood and other fluids from within the heart toward the catheter handle 16.

C. The Mapping Assembly Shaping Mechanism

In the illustrated arrangement, the third mechanism 34 occupies the base 40 of the handle. The proximal end of the control wire 78 of the mapping basket 70 passes through the telescopic shaft for attachment within the steering member 50 (see FIG. 25). The distal end of the control wire 78 is attached to the basket end cap 74 (as FIG. 12 shows).

Fore and aft movement of the steering member 50 along the track 52 thereby axial advances the control wire 78 to move the end cap 74 toward and away from the base member 72. This, in turn, expands, collapses, and shapes the mapping basket 70.

When the steering member 50 occupies the forwardmost position in the track 52 (as FIG. 7 shows), the end cap 74 is spaced farthest away from the base member 74. The flexible electrode support splines 78 lie in a generally linear relationship between the base member 72 and the end cap 74. The mapping basket 70 is in its closed or folded position, as FIG. 7 shows.

When in this position, movement of the sheath control actuator 160 to the forwardmost position in the tip slot 162 will serve to enclose the collapsed mapping basket 70 completely within the sheath 68. The collapsed mapping basket 70 is thereby also retracted (as FIG. 3 shows).

Likewise, movement of the sheath control actuator 160 to its rearwardmost position in the tip slot 162 will move the sheath 68 away from the collapsed mapping basket 70. The mapping basket 70 is thereby deployed (as FIG. 4 shows).

When deployed, movement of the steering member 50 toward the rearwardmost position in the track 52 will move the end cap 74 progressively closer to the base member 72 (as FIGS. 5 and 6 show). The resilient electrode support splines 78 progressively flex to assume a progressively more bowed three dimensional shape. The shape of the mapping basket 70 depends upon the position of the steering member 50 within the track 52.

As the steering member 50 moves from the forwardmost position toward the center position of the track 52 (as FIG. 5 shows), the mapping basket 70 will progressively change from an elongated, oval shape into a spherical shape. As the steering member 50 moves further from the center position toward the rearwardmost position of the track 52, the mapping basket 70 will progressively change from a spherical shape into a donut or toroidal shape.

The third control mechanism 34 preferably includes an external locking nut 166. Clockwise rotation of the locking nut 166 increases the seating force between the steering member 50 and the handle base 40. When moved fully clockwise, the locking nut 166 imposes a seating force that prevents movement of the steering member 50 within the track 52. In this way, the user can lock the mapping basket 70 in the desired shape, while conducting other control or mapping operations.

Counterclockwise rotation of the locking nut 166 decreases the seating force and frees the steering member 50 for movement within the track 52. In this way, the user can manipulate the third mechanism 34 to open, close, and shape the mapping basket 70.

D. The Mapping Assembly 20 Twisting Mechanism

In the illustrated arrangement, the fourth mechanism 36 comprises the rotating junction between the handle base 40 and the handle tip 42. As FIG. 8 shows, by holding the handle tip 42 stationary, the user can rotate the main body 38 of the handle 16 relative to the tip 42. This, in turn, rotates the flexible tube 62, which is attached to the junction tube 46 within the main handle body 38, as FIG. 10 shows. This rotates the mapping basket 70, which is attached to the flexible tube 62, without rotating the sheath (which is separately attached to the carriage 60 within the handle tip 42, as FIG. 11 shows. In this way, the fourth control mechanism 36 rotates the mapping basket 70 without rotating the external sheath 68.

4. Deployable Preshaped Electrode Support Structures

A. Deployable Preshaped Basket Assemblies

It should be appreciated that the mapping assembly 20 just described need not include a control mechanism for altering the basket's shape 70. The basket 70 can be preformed to collapse in response to an external force and to assume a single, prescribed final configuration upon the removal of the external force.

In this arrangement the basket splines 76 are connected between the base member 72 and the end cap 74 in a resilient, pretensed condition. The resilient splines 76 collapse into a closed, compact bundle in response to an external compression force.

In this embodiment, the second control mechanism 32 applies the force to compress the basket 70. Movement of the tip actuator 160 to the forwardmost slot position advances the sheath 68 to compress and collapse the basket 70 while enclosing it. Movement of the tip actuator 160 to rearwardmost slot position advances the sheath 68 away from the basket 70. This removes the compression force, and the freed splines open to assume a prescribed shape. In one preferred arrangement, at least some of the individual splines 78 within the basket 70 include varying regions of stiffness along their length. The varying regions of stiffness deflect differently when commonly stressed. Thus, the spline, when bent, will not assume a uniform arc. Instead, the spline will bend in a nonuniform way, taking on a different shape. By locating splines having regions of varying stiffness in different regions of the array, a multitude of different prescribed shapes for the basket 70 can be obtained.

In another preferred embodiment, at least some of the splines include preshaped memory wire like Nitinol. The memory wire assumes different shapes, depending upon the temperature conditions surrounding it.

In this embodiment, when exposed to room temperature conditions outside the body, the memory wire splines assume a generally straight configuration. In this way, the splines can be collapsed into a compact shape for enclosure within the sheath 68 for placement within a heart chamber. When deployed outside the sheath 68 and exposed to internal body temperatures within the heart chamber, the memory wire splines change their generally straight configuration and assume another predetermined shape.

These different arrays can be attached to the distal end of individual, specialized catheters and be deployed with a handle-mounted control mechanism as previously described.

B. The Deployable Bladder Mapping Assembly

Figure 28:
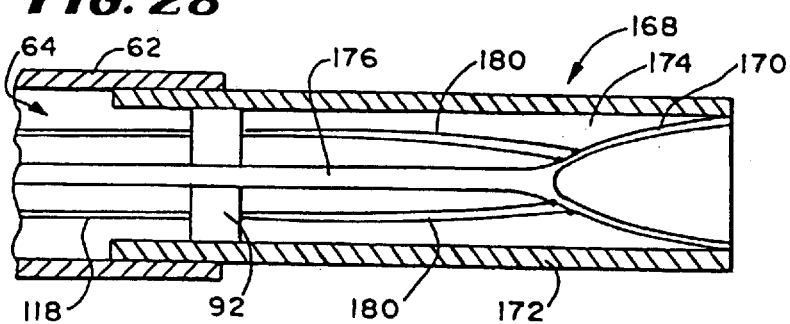
FIGS. 28 and 29 are side section views of an alternative deployable mapping assembly using an inflatable bag.
Figure 29:
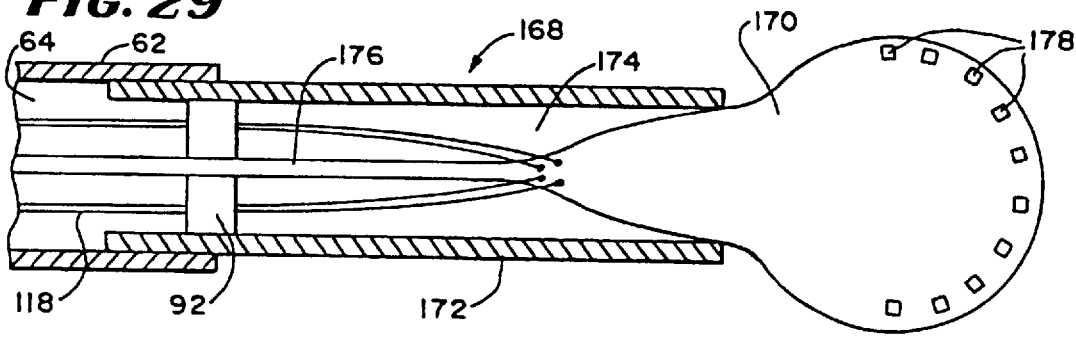

FIGS. 28 and 29 show an alternative mapping assembly 168 in which the support for the sensing electrodes takes the form of an inflatable bladder 170. The inflatable bladder 170 occupies the interior chamber 174 of a base member 172, which the guide tube 62 carries at its distal end. The distal end of the base member 172 is open. As FIG. 28 shows, the bag 170 is normally stored at the distal end of the catheter or within the interior chamber 174 in a deflated, retracted condition.

A fluid pressure conduit 176 communicates with the bag 170. The conduit extends from the interior chamber 174 through the bore 64 of the flexible tube 62 to a port near the probe handle 16 (not shown in FIGS. 28 and 29). In use, the physician connects the port to a source of fluid pressure, such as pressurized carbon dioxide or liquid saline solution.

After maneuvering the distal catheter end to the desired endocardial location, the physician conducts positive fluid pressure through the supply conduit 176 into the bag 170. The positive fluid pressure causes the bag 170 to expand or inflate.

The inflating bag 170 deploys outwardly beyond the open chamber end, assuming a prescribed three dimension shape (as FIG. 29 shows). The shape can vary, depending upon the configuration of the bag. In the illustrated embodiment, the bag 170 assumes a somewhat spherical shape when inflated. Due to its pliant nature, the bag 170, when inflated, naturally conforms to the topography of the endocardial surface that is being mapped.

Release of the positive fluid pressure and the application of negative pressure through the supply conduit 176 will drain fluid from the bag 170. The bag 170 collapses back into the base chamber 174 in a deflated condition (as FIG. 28 shows). Since the bag 170 deploys itself as it inflates, there is no need for a separate control mechanism to deploy the bag.

Alternatively, a movable sheath 68 controlled by the second mechanism 32 (as earlier described) can be used to selectively enclose the bag 170 before use and to free the bag 170 for use.

The bag includes an electrically conducting surface, such as platinum. The surface is applied, for example, using IBAD. The conductive surface can occupy the entire exposed area of the bag 170. In this case, the bag, when inflated, functions as a single sensing electrode 170.

Alternatively, the conductive surfaces can be applied in spaced zones 178 upon the circumference of the bag 170 (as FIG. 29 shows). In this case, each zone 178 acts as an individual sensing electrode. The spaced conductive zones on the bag 170, when inflated, thereby together constitute an array of sensing electrodes. The bag surface also carries a solid state circuit applied by vapor deposition or similar technique. The circuit attached to signal wires 180 to conduct signals from the conductive zones to a microconnector 92 in the base 172. These signals are in turn transmitted along the length of the associated catheter in the manner already described.

C. Deployable Sail Mapping Assembly

Figure 30A:
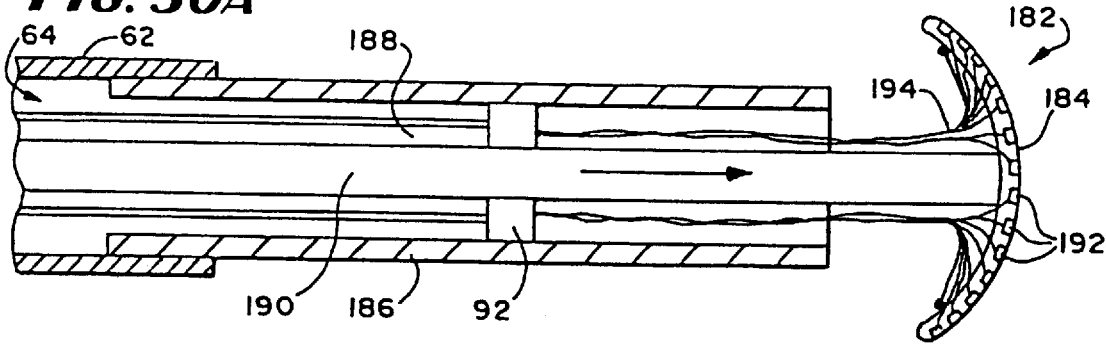
FIGS. 30A and B are side section views of an alternative deployable mapping assembly using a flexible sail-like body.
Figure 30B:
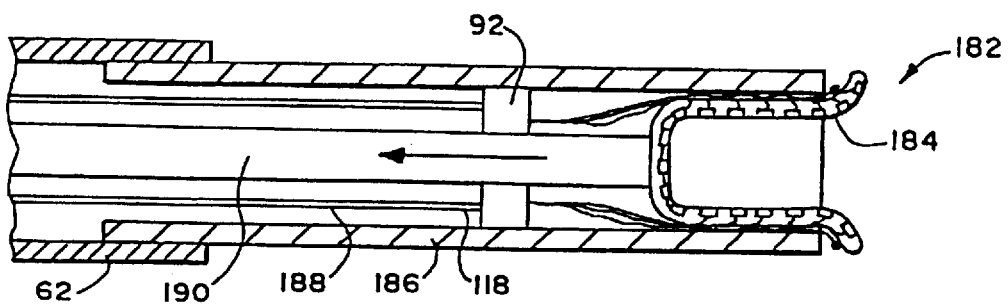

FIGS. 30A and 30B show another alternative mapping assembly 182. In this embodiment, the support for the sensing electrodes takes the form of a resilient body 184 that resembles a sail. The sail body 184 is preferable made of a resilient rubber or elastomeric material.

The assembly 182 includes a base member 186 with an interior chamber 188 having an open distal end. The guide tube 62 carries the base member 186 at its distal end.

A control wire or shaft 190 is attached to the backside of the sail body 184. The control wire 190 is movable along the axis of the guide tube 62 in response to a handle mounted control mechanism, like the control wire 78 associated with the variable size mapping basket shown in FIG. 12. In the illustrated embodiment, the handle mounted control mechanism can affect the same fore and aft movement of the steering member 50 upon the handle base 40, as previously described.

In this arrangement, when the steering member 50 occupies the rearwardmost position in the track 52, the sail body 184 is drawn back within the base chamber 188 (as FIG. 30B shows). In this condition, the sides of the resilient sail body 184 fold forwardly upon the side walls of the chamber 188, and the sail body 184 assumes a folded, concave shape within the confines of the base chamber 188. The mapping assembly 182 is retracted in this condition.

Subsequent movement of the steering member 30 toward the forwardmost position in the track 52 urges the sail body 184 out of the chamber 188. Freed from the confines of the chamber 188, the sides of the sail body 184 resiliently spring into an open, convex shape, as FIG. 30A shows. The mapping assembly 20 is deployed in this condition.

Movement of the steering member 50 back toward the rearwardmost position in the track 52 urges the sail body 184 back into the confines of the base chamber 188. In the process, the resilient sides of the sail body 184 will again fold forwardly against the side walls of the chamber 188.

The sail body carries one or more sensing electrodes 192. The electrodes 192 can be physically attached to the sail body 184. Alternatively, the electrodes can be applied, for example, using IBAD.

The sail electrode array 182 is ideally suited for endocardial mapping. Like the previously described bag array 168 (shown in FIGS. 28 and 29), the deformable, elastic sail body 184 will readily conform to the topography of the endocardial surface that it is pressed against for mapping.

A hard wire or solid state circuit on the sail body 184 attaches to signal wires 194 to conduct signals from the electrodes 194 to a microconnector 92 in the base 186. These signals are in turn transmitted along the length of the catheter in the manner already described.

D. Deployable Radial Bundle Mapping Assembly

FIGS. 31A; 31B; and 31C show yet another alternative mapping assembly 196. In this embodiment, the support for the sensing electrodes includes a center spine 198 from which an array of flexible support filaments radiate. Each support filament carries a sensing electrode 202.

As before, the assembly includes a base 204 with an interior chamber 206 having an open distal end. As before, the guide tube 62 carries the base 204 at its distal end.

The center spine 198 is movable along the axis of the guide tube 62 in response to the operation of a handle mounted control mechanism. In the illustrated embodiment, fore and aft movement of the steering member 50, as previously generally described, can serve this control function.

In this arrangement, when the steering member 50 occupies the rearwardmost position in the track 52, the mapping assembly 200 is retracted and the filament array 196 is drawn back within the base chamber 206, as FIG. 31A shows. In this condition, each filament 200 is folded against the side walls of the chamber 206.

Subsequent movement of the steering member 50 toward the forwardmost position in the track 52 urges the central spine 198 out of the chamber 206. Freed from the confines of the chamber 206, the support filaments 200 spring into an open, three dimensional array radially surrounding the center spine 198, as FIG. 31B shows. The mapping assembly 20 is thus deployed.

Movement of the steering member 50 back toward the rearwardmost position in the track 52 urges the center spine 198 back into the confines of the base chamber 206. In the process, the flexible filaments 200 fold forwardly against the side walls of the chamber 206, as FIG. 31C shows.

The radial bundle of filaments 200, each carrying a sensing electrode 202, offers a high density, random mapping array 196. The flexible nature of the random array 196 readily conforms to the topography of the endocardial surface that it is pressed against.

A hard wire or solid state circuit on the filaments 200 and center spine 198 conducts signals from the individual electrodes 202 to a microconnector 92 in the base 204. These signals are in turn transmitted along the length of the catheter in the manner already described.

E. Deployable Foam Tip Mapping Assembly

FIGS. 32A and 32B show still another alternative mapping assembly 208. In this embodiment, the support for the sensing electrodes takes the form of a porous foam body 210.

As before, the assembly 208 includes a base 212 with an interior chamber 214 having an open distal end. As before, the guide tube 62 carries the base 212 at its distal end.

Like the foregoing alternative embodiments, the foam body 210 is deployed from within the interior chamber 214. The foam body 210 is molded to assume what can be called a normal shape. In the illustrated embodiment (as FIG. 32A shows), the normal uncompressed shape is generally spherical. However, the original uncompressed shape can be rectangular, square, oval, toroid, or virtually any other shape.

Due to its porous, open structure, the body 210 can be collapsed, without damage, by an external compression force into another more compact shape. In the illustrated embodiment (as FIG. 32B shows), the more compact shape is generally cylindrical, to fit within the confines of the base chamber 214. However, other compact shapes can be used. When the external compression force is released, the porous foam body resilient returns to its normal shape.

A control wire or shaft 216 is attached to the foam body 210. The control wire 216 is movable along the axis of the guide tube 62 in response to the operation of a handle mounted control mechanism. In the illustrated embodiment, fore and aft movement of the probe steering member 50 can control the wire.

In this arrangement, when the steering member 50 occupies the rearwardmost position in the track 52, the foam body 210 is drawn back within the base chamber 214, as FIG. 32B shows. The side walls of the base chamber 214 compress and collapse the foam body 210. When so compressed, the foam body 210 conforms to the interior shape of base chamber 214. The mapping assembly 208 is retracted.

Subsequent movement of the steering member 50 toward the forwardmost position in the track 52 urges the foam body 210 out of the chamber 214, as FIG. 32A shows. When freed from the confines of the chamber 214, the foam body 210 opens into its normal uncompressed shape. The mapping assembly 208 is deployed.

Movement of the steering member 50 back toward the rearwardmost position in the track 52 urges the foam body 210 back into the confines of the base chamber 214. The foam body 210 is again compressed into a compact, retracted shape, as FIG. 32B shows.

The foam body 210 carries one or more sensing electrodes 218. The electrodes 218 can be physically attached to the foam body 210. Alternatively, the electrodes 218 can be applied, for example, using IBAD. The sensing electrodes 218 constitute a high density array ideally suited for endocardial mapping.

A hard wire or solid state circuit on the foam body 210 conducts signals from the electrode zones 218 to a microconnector 92 in the base 212. These signals are in turn transmitted along the length of the catheter in the manner already described.

5. Dynamic Mapping Assemblies

FIGS. 33 to 36 show a mapping assembly 220 that dynamically alters its shape to compensate for the compression of the heart chamber in which it is located.

The mapping assembly 220 includes a base member 222 that is attached to the distal end of the guide tube 62, as previously described (see FIG. 34). The mapping assembly 220 includes an array of resilient electrode supports 224. Their proximal ends are attached to the base 222, and their distal ends are attached to a end cap 226.

As described, this mapping assembly 220 is identical to the mapping assembly 20 shown in FIG. 12. As in FIG. 12, the mapping assembly 220 can include a movable sheath 68 and an associated control mechanism 32 for alternatively enclosing and deploying the assembly 220.

During endocardial mapping, the heart muscles continuously expand and contract with the beating of the heart. When deployed, the mapping assembly 220 will thereby be subject to alternate cycles of contraction and expansion. The surface pressure of the sensing electrodes 228 against the moving endocardium can therefore continuously vary, complicating the task of accurately recording the potentials. The sensing electrodes can also slip along the constantly moving endocardial surface.

To counteract this phenomenon, the mapping assembly 220 includes means 230 for continuously urging the sensing electrodes 228 against the endocardium and for maintaining a constant surface pressure, despite contraction and expansion of the heart.

The means 230 can vary. In the illustrated embodiment, the base member 222 includes a tubular body that carries a front movable mount 232 and a fixed rear mount 234 (best shown in FIGS. 33 and 35). The interior side wall 236 of the base member 222 serves as a bearing surface for the movable mount 232. The movable mount 232 carries the proximal ends of the electrode supports 224.

A spring 238 connects the front mount 232 to the rear mount 234. The front mount 232 moves toward the rear mount 234 when the electrode supports 224 experience compression within the heart chamber (as FIGS. 33 and 34 show). The reverse is true when the electrode supports 224 experience contraction within the heart chamber (as FIGS. 35 and 36 show).

Movement of the front mount 232 toward the rear mount 234 compresses the spring 238. When compressed, the spring 238 urges the front mount 232 toward a distal position within the base 22, in which the spring 238 is not compressed.

The mounts 232/234 and spring 238 thereby establish an dynamic junction between the electrode supports 224 and the endocardium. Contraction of the heart chamber surrounding the mapping assembly 220 exerts a compression force on the electrode supports 224. The front mount 232 moves toward the rear mount 224 in response to this compression. The spring 238 serves to dampen and resist this movement, holding the electrodes against the endocardium.

When the heart chamber expands, the spring 238 urges the front mount 232 forward, urging the electrode supports 224 back toward their original shape.

The spring thereby maintains contact between the electrode supports 224 and the surrounding, moving endocardium.

In the illustrated and preferred embodiment, the spring 238 has a fixed spring constant that does not vary with compression. In other words, the spring 238 is a constant force spring.

The constant force spring 238 can take various forms. In the illustrated embodiment (as FIGS. 33 and 35 best show), the spring 238 is a conical spring. When compressed, it exerts a constant force, regardless of the degree of compression.

The constant force 238 spring establishes and maintains a constant surface pressure between the mapping assembly 220 and the surrounding endocardium. The dynamic junction established produces consistently accurate readings during periods of contraction and expansion of the surrounding heart muscle.

It should be appreciated that the dynamic junction can be used in association with mapping assemblies of various sizes and shapes. It is not limited in use with the particular basket mapping assembly 220 shown in FIGS. 33 to 36.

6. Mapping Site Flushing and Coagulation Control

According to another aspect of the invention, the mapping assembly can includes means for conveying fluid to the mapping site.

The fluid can be, for example, saline and be used to flush the mapping site to keep the sensing electrodes free of tissue buildup and blood. The fluid can also be heparin or another anticoagulant and be used to actively reduce the incidence of coagulation during the mapping procedure.

The fluid conveying means can vary. In the embodiment shown in FIG. 12, the mapping assembly 20 includes a flexible central tube 240 surrounding the control wire 78. The tube 240 extends from the end cap 74, through the base member 72 and bore of the flexible tube 62 to a fluid port 242 (like that shown in FIG. 26). Fluid to be conveyed to the site is introduced under pressure through the port 242.

The end cap 74 includes a center channel 244 communicating with the distal end of the tube 240. Fluid conveyed by the tube 240 exits through the channel 244 into the mapping site.

Preferably, the center channel includes a one-way annular valve 246, like that shown in FIG. 27. The valve 246 allows fluid to pass from the tube 240 through the channel 244, but prevents the back flow of fluid in the reverse direction. The valve 246 thereby blocks blood and other fluids present within the heart chamber from entering the tube and the interior regions of the catheter.

Various features of the invention are set forth in the following claims.

What is claimed is:

1. An apparatus for performing an endocardial procedure, comprising:

a flexible catheter having a proximal end and a distal end; and a mapping assembly, the mapping assembly including a plurality of flexible electrode supports, each electrode support having a proximal end and a distal end, wherein the electrode supports are connected at their proximal ends to the catheter and at their distal ends to each other, wherein one of the electrode supports is pre-formed to collapse in response to an external force and to assume a single, prescribed final configuration upon the removal of the external force, the pre-formed electrode support having a generally rectangular cross-section and substantially flat surface having a plurality of substantially flat electrodes disposed thereon.

2. The apparatus of claim 1, wherein the pre-formed electrode support comprises pre-shaped memory wire.

3. The apparatus of claim 1, wherein the pre-shaped memory wire comprises super elastic memory material.

4. The apparatus of claim 1, wherein the pre-formed electrode support further comprises a plurality of electrically conductive paths.

5. An apparatus for performing an endocardial procedure, comprising:

a flexible catheter having a proximal end and a distal end; and a mapping assembly, the mapping assembly including a plurality of flexible electrode supports, each electrode support having a proximal end and a distal end, wherein the electrode supports are connected at their proximal ends to the catheter and at their distal ends to each other, wherein each electrode support is pre-formed to collapse in response to an external force and to assume a single, prescribed final configuration upon the removal of the external force, each pre-formed electrode support having a generally rectangular cross-section and a substantially flat surface having a plurality of substantially flat electrodes disposed thereon.

6. The apparatus of claim 5, wherein each electrode support further comprises a plurality of electrically conductive paths.

7. The apparatus of claim 5, wherein the plurality of flexible electrode supports comprise pre-shaped memory wire.

8. The apparatus of claim 5, wherein at least one of the flexible electrode supports has a longitudinal region of varying stiffness along an axis extending between its proximal and distal ends.

9. The apparatus of claim 5, wherein the respective pre-shaped memory wires each comprise a super elastic memory material.

10. The apparatus of claim 5, wherein the respective pre-shaped memory wires are made of Nitinol.

11. An apparatus for performing an endocardial procedure, comprising:

a flexible catheter having a proximal end and a distal end;

a steering control element attached to the proximal end of the catheter; and a mapping assembly, the mapping assembly including a plurality of flexible electrode supports, each electrode support having a proximal end and a distal end, wherein the electrode supports are connected at their proximal ends to the catheter and at their distal ends to each other, and wherein one of the electrode supports is pre-formed to collapse in response to an external force and to assume a single, prescribed final configuration upon the removal of the external force, the pre-formed electrode support having a generally rectangular cross-section and a substantially flat surface having a plurality of substantially flat electrodes disposed thereon.

12. The apparatus of claim 11, wherein the steering control element comprises a handle having a main body with an interior channel including an annular groove, a junction tube secured within the interior channel, a generally flat base having a steering member which houses at least one control mechanism actuator, and a tip having a flanged end which is rotatably seated within the annular groove of the main body interior channel.

13. The apparatus of claim 11, wherein the pre-formed electrode support comprises pre-shaped memory wire.

14. The apparatus of claim 11, wherein the pre-shaped memory wire comprises super elastic memory material.

15. The apparatus of claim 11, wherein the respective one electrode support further comprises a plurality of electrically conductive paths.

16. An apparatus for performing an endocardial procedure, comprising:

a flexible catheter having a proximal end and a distal end; and a mapping assembly, the mapping assembly including
a base member attached to the distal end of the catheter,
an end cap, and
a plurality of flexible electrode supports, each electrode support having a proximal end and a distal end, wherein the plurality of flexible electrode supports are extended in a circumferentially spaced relationship between the base member and the end cap with their respective proximal ends attached to the base member and their respective distal ends attached to the end cap, wherein each electrode support is pre-formed to collapse in response to an external force and to assume a single, prescribed final configuration upon the removal of the external force, the pre-formed electrode support having a generally rectangular cross-section and a substantially flat surface having a plurality of substantially flat electrodes disposed thereon.

* * * * *